US012629111B2

(12) United States Patent (10) Patent No.: US 12,629,111 B2
Sum et al. (45) Date of Patent: May 19, 2026

(54) MOBILE RADIOLUCENT IMAGING TABLE

(71) Applicant: Stryker Corporation, Kalamazoo, MI (US)

(72) Inventors: Jakob Sum, Trossingen (DE); Michael Grady Boucher, Ayer, MA (US); Heather Michelle Bartlett, Dallas, TX (US); Udo Tockweiler, Immendingen (DE)

(73) Assignee: Stryker Corporation, Portage, MI (US)

( * ) Notice: Subject to any disclaimer, the term of this patent is extended or adjusted under 35 U.S.C. 154(b) by 682 days.

(21) Appl. No.: 18/052,540

(22) Filed: Nov. 3, 2022

(65) Prior Publication Data

US 2023/0140334 A1 May 4, 2023

Related U.S. Application Data

(60) Provisional application No. 63/263,568, filed on Nov. 4, 2021.

(51) Int. Cl.
*A61B 6/04* (2006.01)

(52) U.S. Cl.
CPC .................................. *A61B 6/0407* (2013.01)

(58) Field of Classification Search
CPC ........... A61B 6/00; A61B 6/04; A61B 6/0407; A61B 6/0487; A61B 6/08
See application file for complete search history.

(56) References Cited

U.S. PATENT DOCUMENTS

| 2,076,246 A | | 4/1937 | Nelson | |
| 4,538,289 A | * | 8/1985 | Scheibengraber | ..... G01B 11/27 378/20 |
| 5,525,905 A | * | 6/1996 | Mohapatra | ........... A61B 6/0487 324/318 |

(Continued)

FOREIGN PATENT DOCUMENTS

| EP | 1267743 A2 | 1/2003 |
| EP | 1874256 A2 | 1/2008 |

(Continued)

OTHER PUBLICATIONS

Brainlab. (Jul. 28, 2015) "Airo® Mobile Intraoperative CT—Navigated Spinal Workflow," located at https://www.youtube.com/watch?v=Vv-LZgaeFSY; 2 pages.

(Continued)

*Primary Examiner* — Fredrick C Conley
(74) *Attorney, Agent, or Firm* — Morrison & Foerster LLP

(57) ABSTRACT
A mobile radiolucent table system configurable for medical imaging includes a table pedestal comprising a table base portion and a table support mounted to the table base portion; a platform supported by the table support; a frame translatably mounted to the platform and configured for positioning a patient; and an actuator configured to linearly translate the frame relative to the platform between a fully extended configuration and a fully retracted configuration, wherein in the fully extended configuration, a front edge of the frame projects from the platform at least 1 meter past a front edge of the platform and a front edge of the table base portion, wherein the fully extended configuration is configured for medical imaging.

38 Claims, 14 Drawing Sheets

(56)  References Cited

U.S. PATENT DOCUMENTS

| | | | | |
|---|---|---|---|---|
| 6,955,464 | B1 * | 10/2005 | Tybinkowski | A61B 6/0487 |
| | | | | 108/5 |
| 8,397,323 | B2 | 3/2013 | Skripps et al. | |
| 8,931,125 | B2 * | 1/2015 | Fang | A61B 5/704 |
| | | | | 5/601 |
| 2002/0196906 | A1 | 12/2002 | Mun | |
| 2003/0031301 | A1 | 2/2003 | Longton | |
| 2006/0122502 | A1 * | 6/2006 | Scherch | A61N 5/1049 |
| | | | | 600/426 |
| 2007/0007456 | A1 * | 1/2007 | Dailey | A61B 6/08 |
| | | | | 250/363.05 |
| 2007/0080293 | A1 | 4/2007 | Huber | |
| 2009/0306494 | A1 * | 12/2009 | Scarth | G01R 33/381 |
| | | | | 378/63 |
| 2011/0107515 | A1 * | 5/2011 | Brunker | A61N 5/10 |
| | | | | 5/601 |
| 2011/0119829 | A1 | 5/2011 | Skripps et al. | |
| 2013/0081489 | A1 * | 4/2013 | Fang | A61B 6/0471 |
| | | | | 74/89.34 |
| 2017/0020466 | A1 | 1/2017 | Moulin et al. | |
| 2017/0164912 | A1 | 6/2017 | Hou | |
| 2017/0189720 | A1 * | 7/2017 | Liu | A61N 5/1081 |
| 2020/0397389 | A1 | 12/2020 | Stoutenburgh | |
| 2023/0117250 | A1 * | 4/2023 | Buzzatti | A61B 6/486 |
| | | | | 378/209 |

FOREIGN PATENT DOCUMENTS

| | | | |
|---|---|---|---|
| JP | 2010-94291 | A | 4/2010 |
| WO | 01/76481 | A2 | 10/2001 |
| WO | 2006/110703 | A2 | 10/2006 |

OTHER PUBLICATIONS

Brainlab. (Oct. 21, 2013) "Airo® Mobile Intraoperative CT," located at https://www.youtube.com/watch?v=WcffA7kkO0g; 2 pages.

Brainlab. (Sep. 23, 2015) "Airo® Mobile Intraoperative CT—Technical Animation," located at https://www.youtube.com/watch?v=zUMUI_ahKP8; 2 pages.

Extended European Search Report dated Mar. 13, 2023, directed to EP Application No. 22205509.7; 9 pages.

Northeast Georgia Medical Center. (Dec. 26, 2017) "Airo CT Patient Expectation Video | NGHS," located at https://www.youtube.com/watch?v=rHVK5COLVDc; 2 pages.

Decision to Grant dated Aug. 7, 2025, directed to EP Application No. 22 205 509.7; 2 pages.

Intention to Grant dated Mar. 28, 2025, directed to EP Application No. 22 205 509.7; 6 pages.

Extended European Search Report dated Nov. 27, 2025, directed to EP Application No. 25194927.7; 8 pages.

* cited by examiner

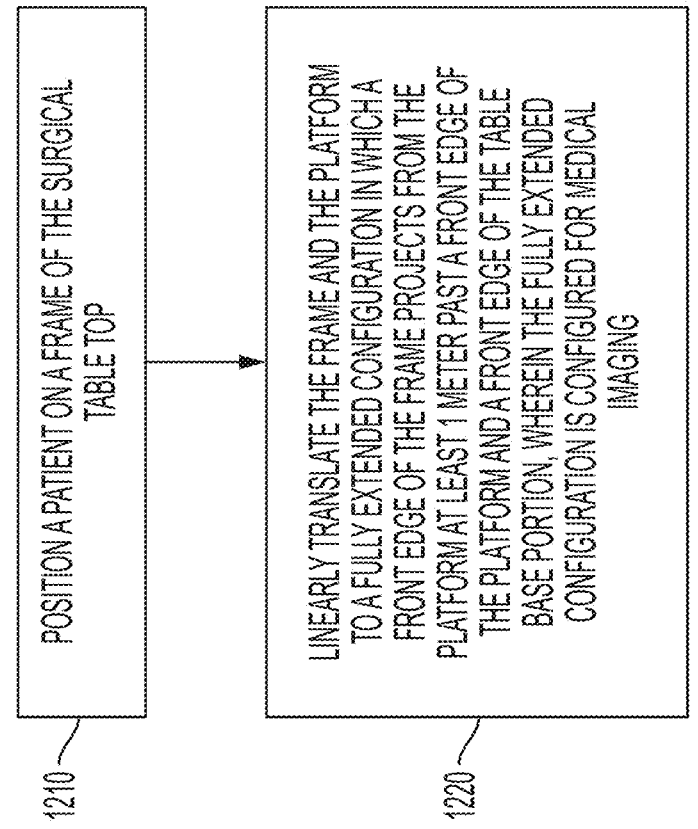

1210    POSITION A PATIENT ON A FRAME OF THE SURGICAL TABLE TOP

1220    LINEARLY TRANSLATE THE FRAME AND THE PLATFORM TO A FULLY EXTENDED CONFIGURATION IN WHICH A FRONT EDGE OF THE FRAME PROJECTS FROM THE PLATFORM AT LEAST 1 METER PAST A FRONT EDGE OF THE PLATFORM AND A FRONT EDGE OF THE TABLE BASE PORTION, WHEREIN THE FULLY EXTENDED CONFIGURATION IS CONFIGURED FOR MEDICAL IMAGING

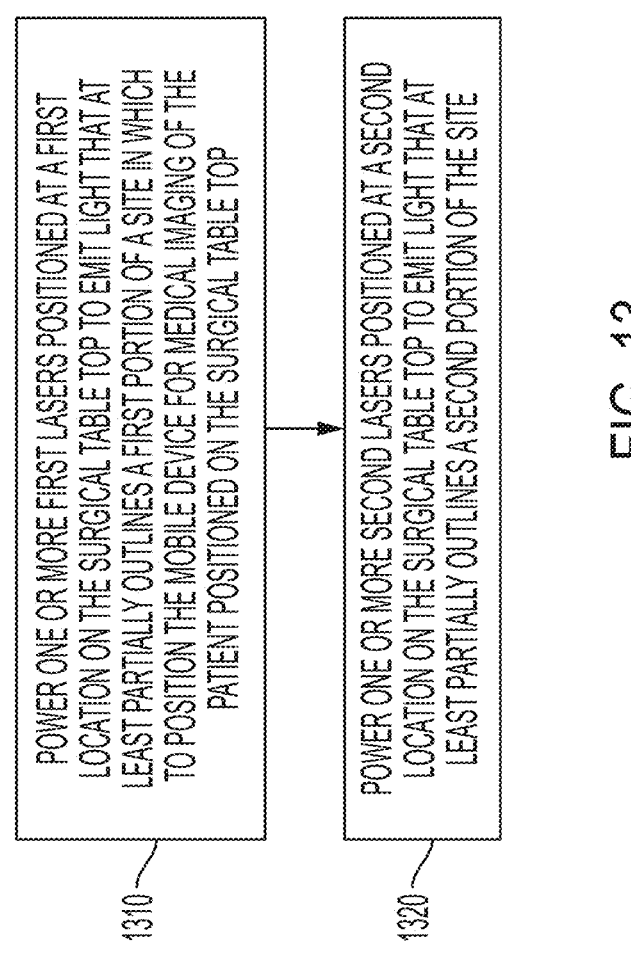

POWER ONE OR MORE FIRST LASERS POSITIONED AT A FIRST LOCATION ON THE SURGICAL TABLE TOP TO EMIT LIGHT THAT AT LEAST PARTIALLY OUTLINES A FIRST PORTION OF A SITE IN WHICH TO POSITION THE MOBILE DEVICE FOR MEDICAL IMAGING OF THE PATIENT POSITIONED ON THE SURGICAL TABLE TOP

1310

POWER ONE OR MORE SECOND LASERS POSITIONED AT A SECOND LOCATION ON THE SURGICAL TABLE TOP TO EMIT LIGHT THAT AT LEAST PARTIALLY OUTLINES A SECOND PORTION OF THE SITE

MOBILE RADIOLUCENT IMAGING TABLE

CROSS-REFERENCE TO RELATED APPLICATIONS

This application claims the benefit of U.S. Provisional Application No. 63/263,568, filed Nov. 4, 2021, the entire contents of which are hereby incorporated by reference herein.

FIELD

This disclosure generally relates to surgical tables, and more specifically to radiolucent surgical tables for imaging and surgery.

BACKGROUND

State of the art medical imaging devices, such as computerized tomography (CT) scanners, have become mobile imaging devices that can be used in various types of locations. Such mobile imaging devices can be transported into an operating room and physically attached to a surgical table for intraoperative medical imaging. The mobile imaging devices include a scanning gantry that translates about the attached surgical table to acquire images of a patient supported on the table.

Typically, once a mobile imaging device is attached to a surgical table for intraoperative imaging, the mobile imaging device remains attached until completion of the surgery. Such attachment prevents relocation of the mobile imaging device during surgery of a first patient, for example, to image a second patient elsewhere.

SUMMARY

According to an aspect, a mobile radiolucent table system is configurable into a self-supported imaging configuration in which a radiolucent patient support is cantilevered at least 1 meter without requiring physical attachment of the mobile radiolucent table system to the mobile imaging device. The imaging configuration is configured to provide a mobile imaging device clearance to scan a patient on the radiolucent patient support. The imaging configuration (also referred to as a fully extended configuration) is useful for intraoperative imaging as it positions the radiolucent patient support frame away from remaining portions of the table system such that a mobile imaging device can scan a length of the radiolucent frame without scanning remaining portions of the table system that could interfere with intraoperative imaging.

According to an aspect, a mobile radiolucent table system configurable for medical imaging includes a table pedestal comprising a table base portion and a table support mounted to the table base portion; a platform supported by the table support; a frame translatably mounted to the platform and configured for positioning a patient; and an actuator configured to linearly translate the frame relative to the platform between a fully extended configuration and a fully retracted configuration, wherein in the fully extended configuration, a front edge of the frame projects from the platform at least 1 meter past a front edge of the platform and a front edge of the table base portion, wherein the fully extended configuration is configured for medical imaging.

Optionally, the mobile radiolucent table system includes one or more counterweights translatably mounted in the platform, wherein projection of the front edge of the frame at least 1 meter past the front edge of the platform and the front edge of the table base portion is balanced by the one or more counterweights attached to the frame and the platform, the one or more counterweights translate relative to the platform based on movement of the frame.

Optionally, the actuator comprises an actuator mechanism attached to the frame and to the one or more movable counterweights, the actuator mechanism comprising at least one or more of a pulley, worm drive, hypoid drive, and rack and pinion, wherein movement of the actuator mechanism is configured to move the one or more movable counterweights in an opposite direction than the frame when the actuator moves the frame relative to the platform.

Optionally, in the fully retracted position the frame does not project from the platform past the front edge of the platform.

Optionally, the platform has a fixed length and maintains the fixed length between the fully extended configuration and the fully retracted configuration.

Optionally, a front portion of the table system includes the front edge of the platform, the front edge of the frame, and the front edge of the table base portion, and the front portion of the table system is configured to face a mobile medical imaging device, wherein in the fully extended configuration the front edge of the frame and the front edge of the platform project past the front edge of the table base portion in a forward direction away from a back portion of the table system, and in the fully retracted configuration the front edge of the frame and the front edge of the platform do not extend past the front edge of the table base portion in the forward direction.

Optionally, the table base portion comprises one or more wheels configured to contact the floor when the table base portion is in an unlocked configuration.

Optionally, the platform comprises a length that is longer than a length of the table base portion that is configured to contact the floor.

Optionally, the frame comprises opposite facing rails and opposite facing end plates that form an opening over which a patient is to be positioned.

Optionally, the frame comprises one or more indicators to mark a length to which a mobile gantry can scan along the frame when the mobile gantry is properly aligned with the mobile radiolucent table system.

Optionally, the frame comprises one or more rails configured to attach one or more accessories for positioning the patient on the frame.

Optionally, the actuator is configured to linearly translate and lock the frame and the platform in any configuration between the fully extended configuration and the fully retracted configuration.

Optionally, the table support is translatable relative to the table base portion.

Optionally, the frame is made of a radiolucent material. Optionally, the radiolucent material is carbon fiber.

Optionally, the frame translatably mounted to the platform, the platform mounted to the table support, and the table support mounted to the table base portion are sized to fit through a standard door opening.

Optionally, the mobile radiolucent table system includes an aligner configured to at least partially outline a site in which to position a mobile gantry for medical imaging of the patient positioned on the frame.

Optionally, the mobile radiolucent table system includes a plurality of lasers configured to emit light that at least partially outlines a site in which to position a mobile gantry for medical imaging of the patient positioned on the frame.

Optionally, the plurality of lasers are positioned at the front edge of the platform on a bottom side or a lateral side of the platform.

Optionally, the plurality of lasers comprises one or more first lasers and one or more second lasers, the one or more first lasers are configured to emit light in a direction perpendicular to the one or more second lasers.

Optionally, the mobile radiolucent table system includes a mobile gantry for medical imaging.

According to an aspect, a surgical table top configurable for medical imaging includes a platform mountable to a table pedestal; a frame translatably mounted to the platform, wherein the frame and the platform are linearly translatable between a fully extended configuration and a fully retracted configuration, and in the fully extended configuration, a front edge of the frame projects from the platform at least 1 meter past a front edge of the platform; and an actuator configured to linearly translate the frame relative to the platform between the fully extended configuration and the fully retracted configuration, wherein the fully extended configuration is configured for medical imaging.

Optionally, the surgical table top includes one or more counterweights translatably mounted in the platform, wherein projection of the front edge of the frame at least 1 meter past the front edge of the platform is balanced by the one or more counterweights attached to the frame and the platform, the one or more counterweights translate relative to the platform based on movement of the frame.

Optionally, the actuator comprises an actuator mechanism attached to the frame and to the one or more movable counterweights, the actuator mechanism comprising at least one or more of a pulley, worm drive, hypoid drive, and rack and pinion, wherein movement of the actuator mechanism is configured to move the one or more movable counterweights in an opposite direction than the frame when the actuator moves the frame relative to the platform.

Optionally, in the fully retracted position the frame does not project from the platform past the front edge of the platform.

Optionally, the platform has a fixed length and maintains the fixed length between the fully extended configuration and the fully retracted configuration.

Optionally, the table pedestal comprises a table base portion and a table support that is mounted to the table base portion, and a front portion of the surgical table top and the table pedestal includes the front edge of the platform, the front edge of the frame, and a front edge of the table base portion, and the front portion is configured to face a mobile medical imaging device, wherein in the fully extended configuration the front edge of the frame and the front edge of the platform project past the front edge of the table base portion in a forward direction away from a back portion of the surgical table top and the table pedestal, and in the fully retracted configuration the front edge of the frame and the front edge of the platform do not extend past the front edge of the table base portion in the forward direction.

Optionally, the table pedestal comprises a table base portion and a table support mounted to the table base portion, the table base portion comprising one or more wheels configured to contact the floor when the table base portion is in an unlocked configuration and configured to be spaced from the floor when the table base portion is in a locked position, and wherein the table support is configured to linearly translate relative to the table base portion.

Optionally, the platform comprises a length that is longer than a length of the table base portion that is configured to contact the floor.

Optionally, the frame comprises opposite facing rails and opposite facing end plates that form an opening over which a patient is to be positioned.

Optionally, the frame comprises one or more indicators to mark a length to which a mobile medical imaging device can scan along the frame when the mobile medical imaging device is properly aligned with the surgical table top.

Optionally, the frame comprises one or more rails configured to attach one or more accessories for positioning the patient on the frame.

Optionally, the actuator is configured to linearly translate and lock the frame and the platform in any configuration between the fully extended configuration and the fully retracted configuration.

Optionally, the frame is made of a radiolucent material. Optionally, the radiolucent material is carbon fiber.

Optionally, the surgical table top and the table base are sized to fit through a standard door opening.

Optionally, the surgical table top includes an aligner configured to at least partially outline a site in which to position a mobile gantry for medical imaging of the patient positioned on the frame.

Optionally, the surgical table top includes a plurality of lasers configured to emit light that at least partially outlines a site in which to position a mobile gantry for medical imaging of the patient positioned on the frame.

Optionally, the plurality of lasers are positioned at the front edge of the platform on a bottom side or a lateral side of the platform.

Optionally, the plurality of lasers comprises one or more first lasers and one or more second lasers, the one or more first lasers are configured to emit light in a direction perpendicular to the one or more second lasers.

According to an aspect, a method of using a surgical table top configurable for medical imaging and mountable to a table pedestal, the table pedestal comprising a table base portion and a table support attached to the table base portion, includes: positioning a patient on a frame of the surgical table top, the frame is translatably attached to a platform of the surgical table top and the platform is mounted on the table support, wherein a centerline of the table support is closer to a front end of the table base portion compared to a back end of the table base portion; and linearly translating the frame relative to the platform to a fully extended configuration in which a front edge of the frame projects from the platform at least 1 meter past a front edge of the platform and a front edge of the table base portion, wherein the fully extended configuration is configured for medical imaging.

Optionally, one or more counterweights are translatably mounted in the platform, and the method comprises balancing projection of the front edge of the frame at least 1 meter past the front edge of the platform and the front edge of the table base portion by translating the one or more counterweights relative to the platform based on movement of the frame.

Optionally, translating one or more counterweights in the platform in an opposite direction than the frame.

Optionally, retracting the front edge of the frame in a backward direction to a fully retracted configuration in which the frame does not project from the platform past the front edge of the platform.

Optionally, the table base portion comprises one or more wheels configured to contact the floor when the table base portion is in an unlocked position and configured to be spaced from the floor when the table base portion is in a locked position.

Optionally, a front portion of the surgical table top and the table pedestal includes the front edge of the platform, the front edge of the frame, and the front edge of the table base portion, and the method comprising positioning the front portion to face a mobile medical imaging device, wherein in the fully extended configuration the front edge of the frame and the front edge of the platform project past the front edge of the table base portion in a forward direction away from a back portion of the surgical table top and the table pedestal, and in the fully retracted configuration the front edge of the frame and the front edge of the platform do not extend past the front edge of the table base portion in the forward direction.

Optionally, the method includes powering a plurality of lasers to at least partially outline a site for positioning a mobile gantry at the front end of the table base portion.

Optionally, the method includes positioning a mobile gantry at the front end of the table base portion.

Optionally, the method includes attaching one or more accessories to one or more rails of the frame for positioning the patient on the frame.

Optionally, the table support is translatably attached to the table base portion.

According to an aspect, an alignment system of a surgical table top that is mountable to or mounted to a table pedestal and configured for positioning a patient on the surgical table top includes one or more first lasers positioned at a first location on the surgical table top and configured to emit light to at least partially outline a first portion of a site in which to position a mobile device for medical imaging of the patient positioned on the surgical table top; and one or more second lasers positioned at a second location on the surgical table top and configured to emit light to at least partially outline a second portion of the site.

Optionally, the one or more second lasers are configured to emit light in a direction perpendicular to the one or more first lasers.

Optionally, the first location and the second location are one or more of a bottom side and a front edge of the surgical table top, wherein the front edge of the surgical table top is configured to be positioned closer to the medical imaging device than a back edge of the surgical table top opposite the front edge.

Optionally, the site comprises a first mark that indicates a first distance to space the mobile imaging device from the surgical table top.

Optionally, the surgical table top comprises an alignment mark, wherein movement of the mobile imaging device to the first distance allows a scan length of the mobile device from the front edge of the surgical table top to the alignment mark on the surgical table top.

Optionally, the table pedestal comprises a table base portion and table support mounted to the table base portion, and the surgical table top comprises a platform mounted to the table support and a frame translatably mounted to the platform.

According to an aspect, a method for aligning a mobile imaging device to a surgical table top that is mountable to or mounted to a table pedestal and configured for positioning a patient includes: powering one or more first lasers positioned at a first location on the surgical table top to emit light that at least partially outlines a first portion of a site in which to position the mobile device for medical imaging of the patient positioned on the surgical table top; and powering one or more second lasers positioned at a second location on the surgical table top to emit light that at least partially outlines a second portion of the site.

Optionally, the method includes positioning the mobile imaging device in the site.

Optionally, the one or more second lasers are configured to emit light in a direction perpendicular to the one or more first lasers.

Optionally, the first location and the second location are one or more of a bottom side and a front edge of the surgical table top, wherein the front edge of the surgical table top is configured to be positioned closer to the medical imaging device than a back edge of the surgical table top opposite the front edge.

Optionally, the site includes a first mark that indicates a first distance to space the mobile imaging device from the surgical table top, and the method comprising moving the mobile imaging device towards the surgical table top to the first mark.

Optionally, the surgical table top comprises an alignment mark, wherein movement of the mobile device to the first mark allows a scan length of the mobile device from the front edge of the surgical table top to the alignment mark on the surgical table top.

Optionally, the method includes positioning a patient on the surgical table top.

Optionally, the table pedestal includes a table base portion and table support mounted to the table base portion, and the surgical table top comprises a platform mounted to the table support and a frame translatably mounted to the platform.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The disclosure will now be described, by way of example only, with reference to the accompanying drawings, in which:

FIG. 12 shows an exemplary flow chart that describes a method for using a surgical table top configurable for medical imaging and mountable to a table pedestal.

FIG. 13 shows an exemplary flow chart that describes a method for aligning a mobile imaging device to a surgical table top.

DETAILED DESCRIPTION

Figure 1:
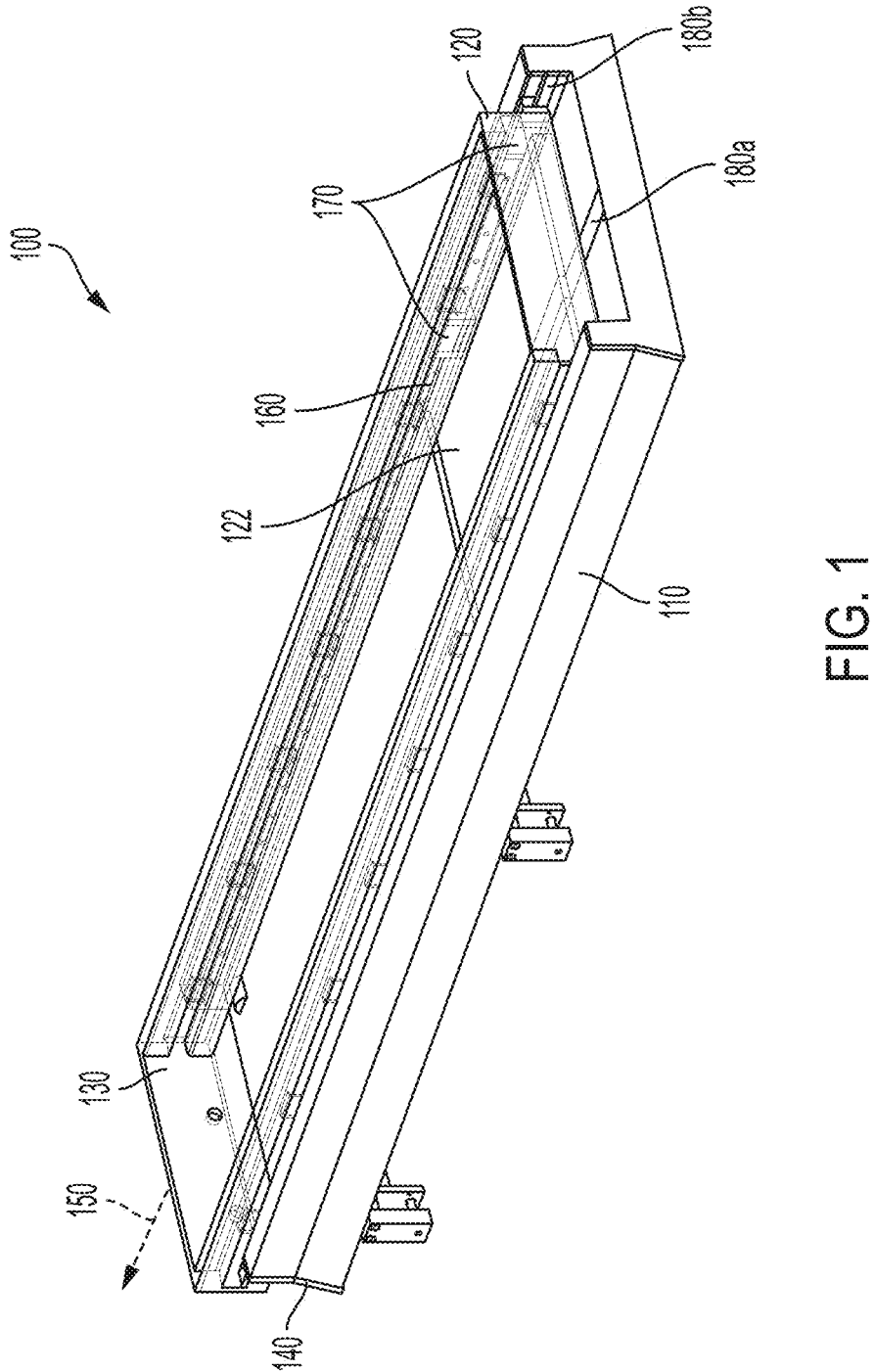
FIG. 1 shows an example of a table top configured to support a patient.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Devices, systems, and methods according to various examples described herein include a table system that includes a platform and a patient support frame configurable into an imaging configuration (also referred to as a fully extended configuration) in which the frame projects at least 1 meter past a front edge of the platform. The projection of the frame at least 1 meter past the front end of the platform allows a mobile imaging device aligned to the table system to complete a scan of 1 meter or more, which can encompass an entire length of a spine of a patient positioned on the frame. The table system does not require physical attachment to a mobile imaging device to balance projection of the frame past the front edge of the platform.

The projection of the frame at least 1 meter past the front end of the platform allows an imaging field of view that includes the frame, but excludes other components of the table system which may or may not be radiolucent—providing an unobstructed image of the patient with minimal interference. Such unobstructed intraoperative imaging provides increased precision and patient safety during spinal surgeries, particularly on patients having large scoliosis or other deformities.

Furthermore, since the table system does not require attachment to a mobile imaging device for intraoperative imaging, a mobile imaging device may be moved to and from the table system as needed without disrupting surgery. For example, in a case where intraoperative imaging is needed during a first part of surgery, but not during a second part of surgery—the mobile imaging device may be aligned to the table system for intraoperative imaging during the first part of surgery and then moved away from the table system during the second part of surgery. In this way, the mobile imaging devices can be moved as needed from patient to patient or room to room increasing the utility of the mobile imaging device.

According to some examples, the platform and the patient support frame form a table top configurable into a plurality of configurations ranging from a fully retracted configuration to a fully extended configuration. In the fully extended configuration, a front end of the frame extends at least 1 meter past a front edge of the platform in a forward direction. In the fully retracted configuration, the front end of the frame does not extend past the front end of the platform in the forward direction.

The table top may be mounted onto compatible table pedestals. Compatible table pedestals may include table pedestals for surgical tables configured to support weight of the table top and of a patient. Mounting the table top onto a compatible table pedestal enables various configurations for positioning a patient for surgery, imaging, or a combination thereof and does not require that a mobile imaging device support or attach to the table top or table pedestal. That is, configuration of the table top into the various configurations described herein can be achieved independent of a mobile imaging device. Since neither the table top nor the table pedestal requires support from a mobile imaging device, the mobile imaging device may operate independent of the table top and the table pedestal which allows the mobile imaging device to be easily moved to and from the table top as needed during surgery. According to some examples, a table comprising a table pedestal compatible with the table top may be upgraded with the table top described herein by dismounting a previous table top (if any) and mounting the table top described herein comprising the patient support frame and the platform.

A table system may include the table top and the compatible table pedestal and the table top on the compatible table pedestal can be configurable into a plurality of configurations ranging from the fully retracted configuration to the fully extended configuration. According to some examples, the compatible table pedestals can include a table base portion configured for contacting the floor and a table support attached to the table base portion and the table top. The configurations of table top mounted on the compatible table pedestal can be distinguished from each other based on a positioning of the frame, the platform, and the table system at a front end of the table system. The front end of the table system can include a front edge of the frame, a front edge of the platform, and a front edge of a table pedestal. In the fully extended configuration, the front end of the frame extends at least 1 meter past the front edge of the platform and the front edge of the table pedestal in a forward direction. In the fully retracted configuration, the front end of the frame does not extend past the front end of the platform and the front end of the table pedestal in the forward direction. While the table system is in the fully retracted configuration, mobile imaging devices can be driven close to the front end of the table system for alignment of the mobile imaging device to the table system.

A table system may include the table top and a dedicated table pedestal configured to permanently support the table top (i.e., the table top and table pedestal are not designed to be separated in the field). According to some examples, the dedicated table pedestal can include a table base portion configured for contacting the floor and a table support attached to the table base portion and the table top. Similar to the compatible table pedestals described above, the configurations of table top mounted on the compatible table pedestal can be distinguished from each other based on a positioning of the frame, the platform, and the table system at a front end of the table system. The table support can include a top end attached to the platform of the table top and a bottom end opposite the top end attached to the table base portion. According to some examples, the top end can include sidewalls that slant inward and secure the platform to the table support. According to some examples, the table support may be translatably attached to the table base portion. In this way, the table support, the platform, and the frame can be translated together relative to the table base portion.

The frame translatably mounted to the platform, the platform mounted to the table support, and the table support mounted to the table base portion can be sized to fit through a standard door opening. In this way, the table system that includes the table top mounted to a table pedestal can be maneuvered between rooms without requiring disassembly.

The table top can include at least one actuator for controlling translation of the frame relative to the platform between the fully extended configuration and the fully retracted configuration. According to some examples, the at least one actuator may be configured to secure the frame in a locked configuration. In some variations, the at least one actuator includes a self-locking feature, such as a self-locking lead screw. The at least one actuator may be operated via remote control. In some examples, the platform can be translatably attached to a portion of the table pedestal. In some examples, at least one first actuator translates the platform relative to the table pedestal and at least one second actuator translates the frame relative to the platform.

The table top may include one or more counterweights mounted in the platform and attached to the frame for balancing the frame and the platform in various configurations. According to some examples, the one or more counterweights balance the frame and the platform by moving along a length of the platform in a direction that is opposite to a movement direction of the frame when the frame moves. The one or more counterweights may be attached to the frame by at least one actuator mechanism, such as a pulley, worm drive, hypoid drive, and rack and pinion that allows movement of the one or more counterweights when there is movement of the frame. According to some examples, the one or more counterweights balance the frame and the platform by remaining fixed in the platform at a position where the one or more counterweights balance a full extension range of the frame from the platform. The one or more counterweights may be made of a suitable material, such as steel.

According to some examples, a range of travel of the frame is over 1 meter in both a forward direction for moving the frame into the fully extended configuration and a reverse direction for moving the frame into fully retracted configuration. According to some examples, the range of travel of the frame in the forward and reverse directions may be at least 1 meter, or at least 1.1 meters, or at least 1.2 meters. According to some examples, the range of travel of the frame in the forward and reverse directions may be at most 2 meters, or at most 1.6 meters, or at most 1.4 meters. According to some examples, the range of travel of the frame in the forward and reverse directions may be 1 meter to 2 meters, or 1.1 meters to 1.6 meters, or 1.2 meters to 1.4 meters.

According to some examples, a range of travel of the one or more counterweights in response to movement of the frame is the same as a range of travel of the frame. According to some examples, a range of travel of the one or more counterweights is over 1 meter in both the forward direction and the reverse direction. According to some examples, the range of travel of the one or more counterweights in the forward and reverse directions in response to movement of the frame may be at least 1 meter, or at least 1.1 meters, or at least 1.2 meters. According to some examples, the range of travel of the one or more counterweights in the forward and reverse directions in response to movement of the frame may be at most 2 meters, or at most 1.6 meters, or at most 1.4 meters. According to some examples, the range of travel of the one or more counterweights in the forward and reverse directions in response to movement of the frame may be 1 meter to 2 meters, or 1.1 meters to 1.6 meter, or 1.2 meters to 1.4 meters.

According to some examples, a range of the table support relative to the table base portion may be at least 100 millimeters, or at least 200 millimeters, or at least 300 millimeters. According to some examples, a range of the table support relative to the table base portion may be at most 700 millimeters, or at most 600 millimeters, or at most 500 millimeters. According to some examples, a range of the table support relative to the table base portion may be 100 millimeters to 700 millimeters, or 200 millimeters to 600 millimeters, or 300 millimeters to 500 millimeters.

According to some examples, a length of the platform may be at least 1 meter, or at least 1.5 meters, or at least 2 meters. According to some examples, a length of the platform may be at most 3.5 meters, or at most 3 meters, or at most 2.5 meters. According to some examples, a length of the platform may be 1 meter to 3.5 meters, or 1.5 meters to 3 meters, or 2 meters to 2.5 meters. According to some examples, a length of the platform may be longer than a length of a base of the table pedestal. According to some examples, a platform may have a fixed length and the fixed length may be maintained throughout the various configurations of the table top.

According to some examples, a length of the frame translatably attached to the platform may be at least 1 meter, or at least 1.5 meters, or at least 2 meters. According to some examples, a length of the platform may be at most 3.5 meters, or at most 3 meters, or at most 2.5 meters. According to some examples, a length of the platform may be 1 meter to 3.5 meters, or 1.5 meters to 3 meters, or 2 meters to 2.5 meters.

The table top may include an alignment system configured to indicate where a mobile imaging device should be positioned to align to the table top on a table pedestal (either a compatible or a dedicated table pedestal). The position in which the mobile imaging device should be positioned for alignment to the table top or to a table system will be referred herein as a "parking spot". Positioning of the mobile imaging device in the parking spot designated by the alignment system does not require physical attachment between the mobile imaging device and the table top or the table pedestal (or collectively the table system). According to some examples, the alignment system at least partially outlines the parking spot via alignment marks on the ground that indicate to a driver of the mobile imaging device exactly where and how the mobile imaging device should be positioned. In this way, the alignment system allows the mobile imaging device to be aligned with precision and repeatability, and without physical attachment to the table system. According to some examples, once the mobile imaging device is in the parking spot and the patient support frame is in one of the extended configurations, then a user can operate the mobile imaging device to initiate a scan of the patient on the patient support.

The alignment system may indicate at least a partial perimeter of the parking spot. The partial perimeter may be, for example, one or more two parallel lines or two perpendicular lines. According to some examples, the parking spot may form at least part of a grid. According to some examples, the alignment system may include one or more light sources to indicate where a mobile imaging device should be positioned to align to the table top and the table pedestal (or collectively the table system). According to some examples, the alignment system may include one or more lasers for indicating where a mobile imaging device should be positioned to align to the table system. The one or more lasers may be positioned on a front end of the table system that is configured to face a mobile imaging device.

The table top can include a plurality of lasers for indicating where a mobile imaging device should be positioned to align to the table system. The plurality of lasers can include one or more first lasers and one or more second lasers. The one or more second lasers may be configured to shine light in a direction perpendicular to light from the one or more first lasers.

According to some examples, an alignment system described herein allows a user to position the front end of the table system an optimal distance away from the mobile imaging device. During alignment, the table top of the table system may be configured into the fully retracted configuration to allow clearance for a mobile imaging device to align close to the table system. The optimal distance allows enough clearance between the mobile imaging device and the front end of the table system for setting up the mobile imaging device without contacting one or more of the table system and the patient. According to some examples, the optimal distance may be at least 6 inches, or at least 8 inches, or at least 10 inches. According to some examples, the optimal distance may be at most 24 inches, or at most 20 inches, or at most 15 inches. According to some examples, the optimal distance may be at 6 inches to 24 inches, or at 8 inches to 20 inches, or at 10 inches to 15 inches.

The frame may include one or more marks that indicate a length to which a mobile imaging device properly aligned to the table system can scan along the frame. For example, when a mobile imaging device is positioned in the position indicated by the alignment system, the mobile imaging device can conduct a scan up to the one or more marks indicated on the frame. Thus, prior to alignment of the mobile imaging device, a medical professional can use the one or more marks to determine how to position a patient on the frame such that an anatomical area of interest would be within a field of view of a mobile imaging device aligned to the table system.

The accessories may be mounted onto the frame for supporting and positioning a patient on the frame. The accessories allow customizable patient support and patient positioning tailored to a patient's medical needs and body and the surgeon's procedural preference. Such customization allows a surgeon flexibility in accessing surgical sites of the patient. For example, in some cases, a surgeon may need to position a patient on the frame such that the patient's head is located at a front end or a back end of the frame. The accessories may be modularly mounted to position the patient comfortably in either orientation.

Accessories may include, for example, a head support, chest support, hip support, thigh support, leg support, arm support, leg sling, curved torso support, and skull clamp. A user of the table system may mount the accessories as needed along edges of the frame by latching each accessories individually onto the frame. The accessories may be mounted in a modular fashion as needed to customize patient support and position based on a patient's need. According to some examples, accessories may be mounted such that a patient's abdomen hangs freely. Abdomen hang is key for reduction of fluid loss, access to the spine, and movement of the upper body. According to some examples, the accessories can be radiolucent.

In addition, it is also to be understood that the singular forms "a", "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

FIG. 1 shows an example of a table top configured to support a patient. In the example of FIG. 1, the table top 100 includes a platform 110 mountable to a table pedestal and a frame 120 translatably attached to the platform 110. The table top 100 is configurable into various configurations as needed to support a patient for medical imaging, surgery, pre- and post-surgery procedures, or transportation within a facility. For example, the frame 120 can be translated relative to the platform 110 from a fully retracted configuration, which can be useful when maneuvering a mobile imaging device into position, to a fully extended configuration for intraoperative medical imaging, and configurations therebetween. In each configuration, a front end portion of the frame 120 can be positioned in a different translational position relative to the platform 110. For example, in the fully retracted configuration, a front end portion 130 of the frame 120 may be positioned flush with or retracted from a front end portion 140 of the platform 110. In the fully extended configuration, the front end portion 130 of the frame 120 may be positioned at least 1 meter past the front end portion 140 of the platform 110 in a forward direction indicated by dashed arrow 150 in FIG. 1.

The platform and the frame can be attached via corresponding rails and carriages. In the example of FIG. 1, the platform 110 includes rails 160 and the frame 120 includes carriages 170 that are configured to attach to the rails 160 of the platform such that upon actuation of the frame 120, the carriages 170 slide along the rails 160 of the platform. According to some examples, the platform 110 may include one or more tracks 180a, 180b configured to receive a portion of the frame 120 or rails 160 of the platform. In alternate examples, the frame can include rails and the platform can include carriages configured to attach to the rails of the frame.

Figure 2:
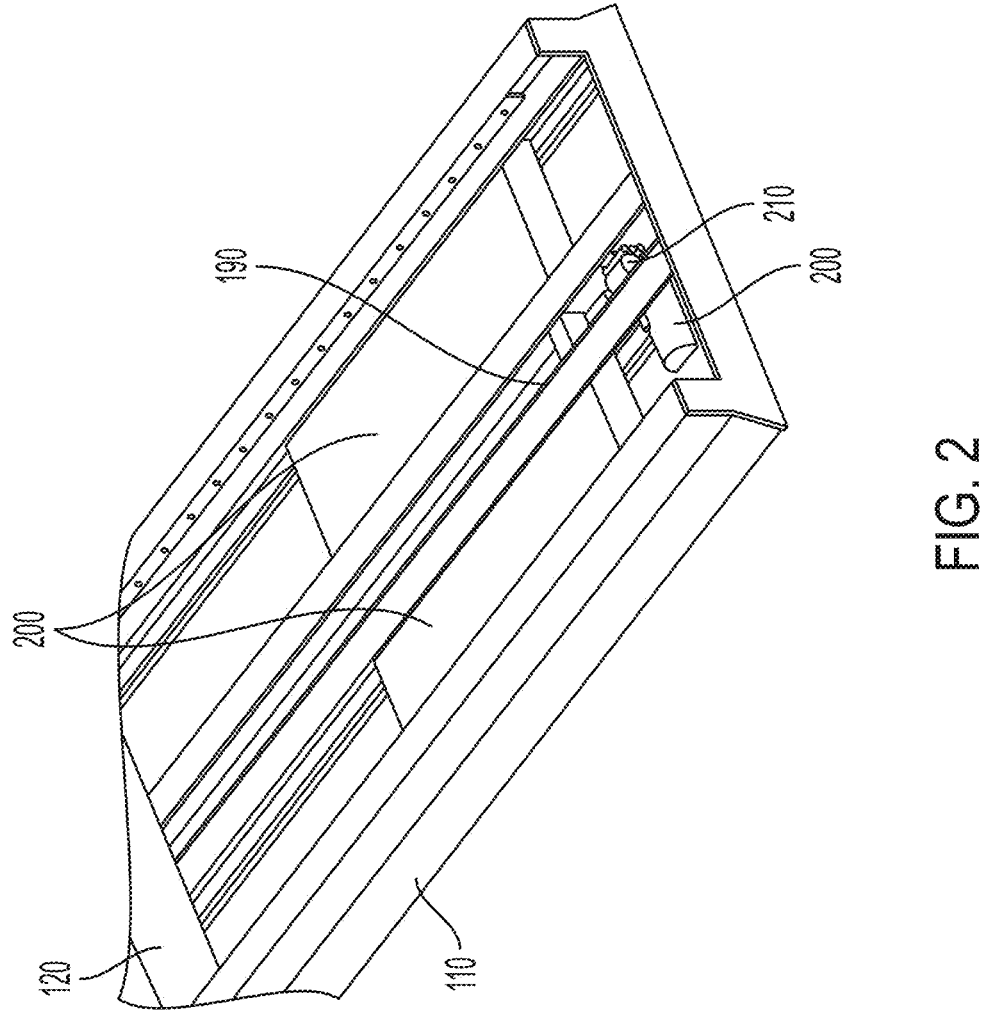
FIG. 2 shows an example of an actuator of a table top.

The table top 100 can include at least one actuator that is attached to one or more of the platform 110 and the frame 120 for translating the frame 120 relative to the platform 110 between various configurations. The following description refers to a single actuator for simplicity and it should be understood that any number of actuators can be used. According to some examples, the actuator can be attached to a base plate 122 of the frame and to the platform 110, such as to track 180a of the platform 110. FIG. 2 shows an example of an actuator of a table top. In the example of FIG. 2, the actuator includes a threaded shaft 190 rotatably attached to the platform 110 and a shaft nut (not shown) attached to the frame 120. Rotation of the threaded shaft 190 causes translation of the shaft nut, which moves the frame 120 between the fully retracted configuration and the fully extended configuration. According to some examples, a drive motor 200 interconnected to a gear box 210 can drive the threaded shaft 190.

One or more counterweights can be used to balance the frame in all table top configurations. In the example of FIG. 2, one or more counterweights 200 are positioned in the platform 110 and attached to the frame 120. According to some examples, the one or more counterweights 200 may be configured to translate in the platform 110 in response to the frame moving between configurations. To balance the frame 120 in any configuration, the one or more counterweights 200 may be configured to move in an opposite direction of the frame 120. For example, as the frame 120 moves in the forward direction indicated by arrow 150, the one or more counterweights 200 can move in a direction opposite the forward direction at the same time. In this way, the one or more counterweights 200 can be positioned in an appropriate position in the platform 120 that balances extension and retraction of the frame 120. The translational movement of the one or more counterweights 200 may be driven by an actuator mechanism of an actuator configured to translate the frame 120. The actuator mechanism can be, for example one or more of a pulley, worm drive, hypoid drive, and rack and pinion.

Figures 3A, 3B:
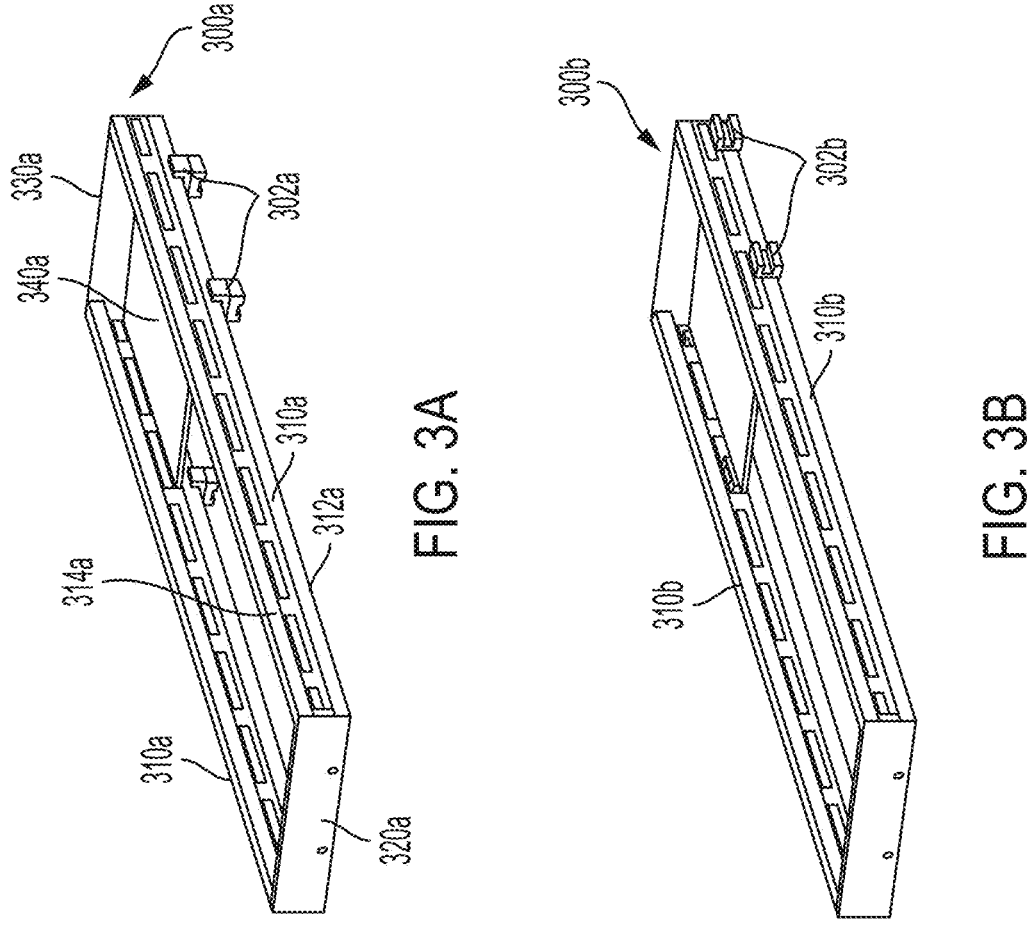
FIG. 3A shows an example of a frame that includes a plurality of carriages positioned on a bottom side of the frame.
FIG. 3B shows an example of a frame that includes a plurality of carriages positioned on a lateral side of frame.

A frame can include a plurality of carriages configured to track a rail of a platform such that the frame can translate relative to the platform along the rails of the platform. For example, FIG. 3A shows a frame 300a that includes a plurality of carriages 302a positioned on a bottom side of the frame 300a. FIG. 3B shows an example of a frame 300b that is similar to 300b, however, frame 300b includes a plurality of carriages 302b positioned on a lateral side of frame 300b.

The frame may include rails configured according to a suitable industry standard such that one or more off-the-shelf accessories can be attached to the frame. FIGS. 3A and 3B show examples of a suitable frame for supporting a patient. For brevity, since the frame structure of frames 300a and 300b differ only in the plurality of carriages 302a, 302b, the remaining frame structure will be discussed in reference to frame 300a. As shown in FIG. 3A, frame 300a includes side rails 310a, a front end plate 320a, a back end plate 330a, and a bottom plate 340a. Each rail 310a can include a plurality of stacked bars. For example, rails 310a each include stacked bars 312a, 314a. The bars 312a, 314a are configured for mounting accessories for positioning a patient on the frame. The accessories can latch onto either one or more of the stacked bars 312a, 314a. The rails 310a at opposite ends can be connected by the front end plate 320a and the back end plate 330a. The bottom plate 340a can be configured to provide a surface of the frame 300a onto which an actuator positioned in a platform for translating the frame can attach to the frame 300a.

A structure of the frame 300a formed by the side rails 310a, the front end plate 320a, the back end plate 330a, and the bottom plate 340a can be configured to support a patient on the frame 300a while allowing a patient's abdomen to hang freely through an opening in the frame structure. The bottom plate 340a can extend from one rail 310a to an opposite rail 310a and extend partially between the front end plate 320a and the back end plate 330a. By configuring the frame 300a in this way, a patient can be supported on the frame 300 such that the patient's abdomen can hang freely within the frame 300. Abdomen hang allows for reduction of fluid loss in the patient, access to the spine, and movement of the patient's upper body, and thus is important during surgery and intraoperative imaging.

Figure 4:
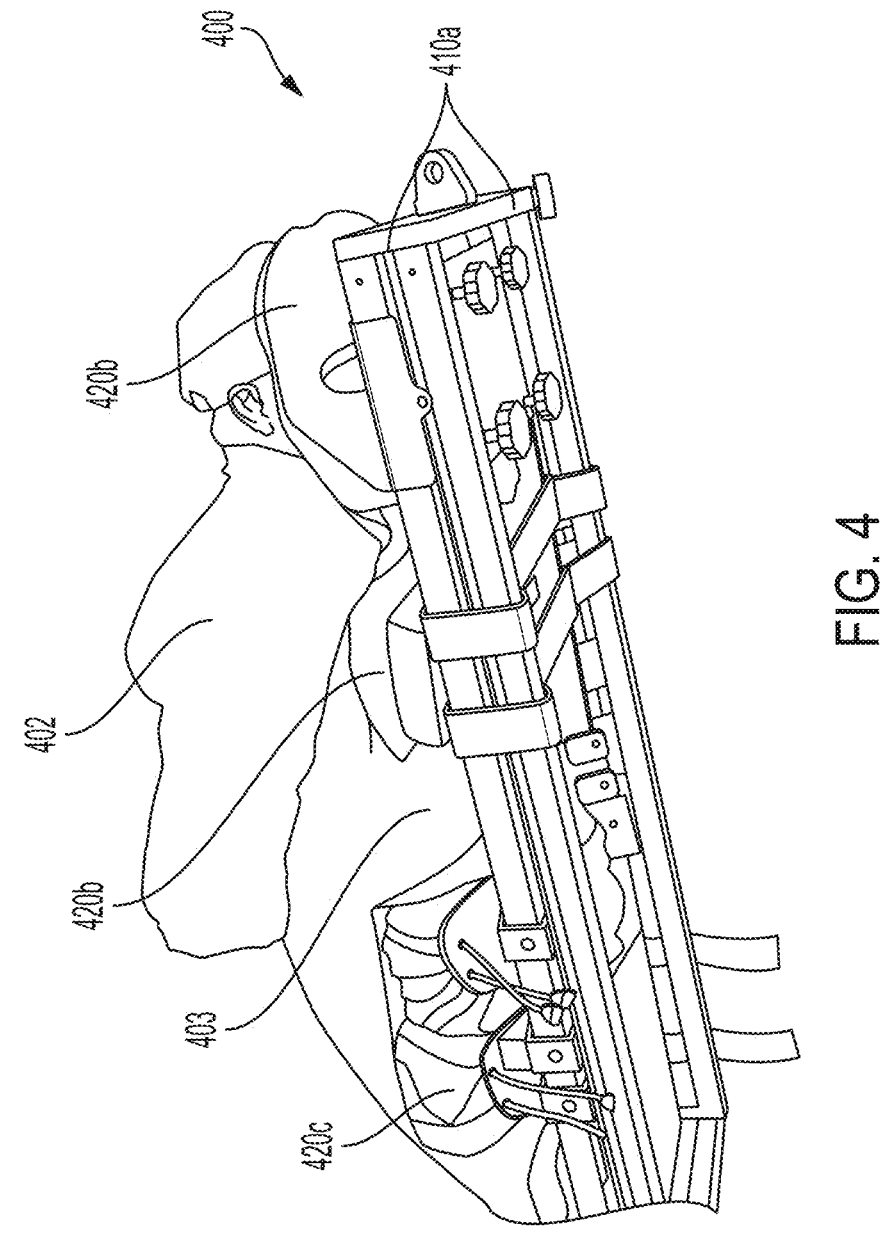
FIG. 4 shows an example of a frame that is configured to allow a patient's abdomen to hang freely and includes accessories for positioning a patient on the frame.

FIG. 4 shows an example of a frame that is configured to allow a patient's abdomen to hang freely and includes accessories for positioning a patient on the frame. In the example of FIG. 4, a frame 400 includes rails 410 and accessories 420 secured to the rails 410 for positioning a patient 402 onto the frame. The accessories 420 can include a head support 420a, a chest support 420b, and a hip support 420c. As shown in FIG. 4, the frame 400 with its accessories 420 is configured to allow the patient's abdomen 403 to hang freely. According to some examples, the accessories can be modular such that the accessories can be exchanged and positioned on the rails as needed for a patient. According to some examples, one or more of the frame and the accessories can be radiolucent.

Figure 5A:
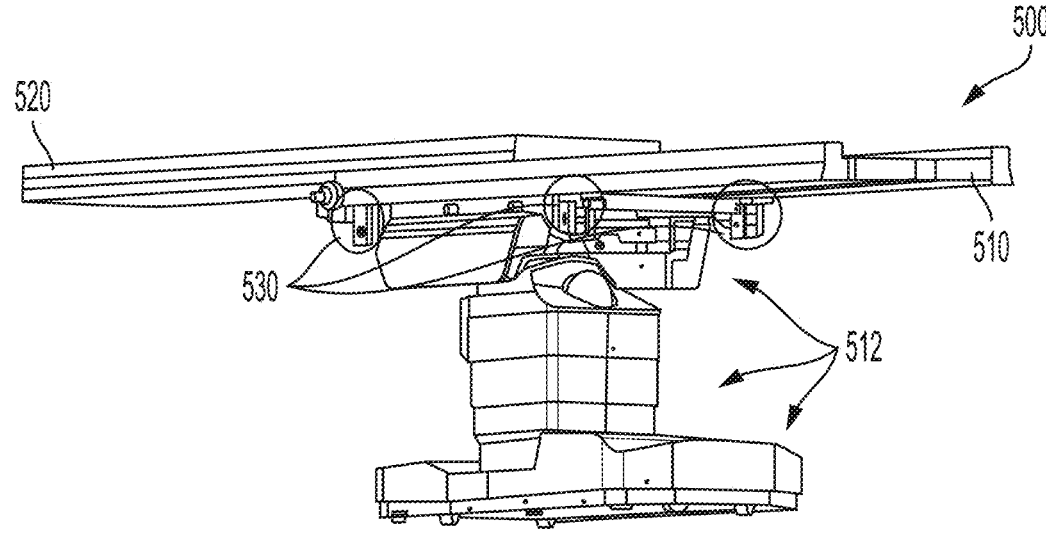
FIG. 5A shows an example of a table system comprising a platform mounted to a compatible table pedestal.
Figure 5B:
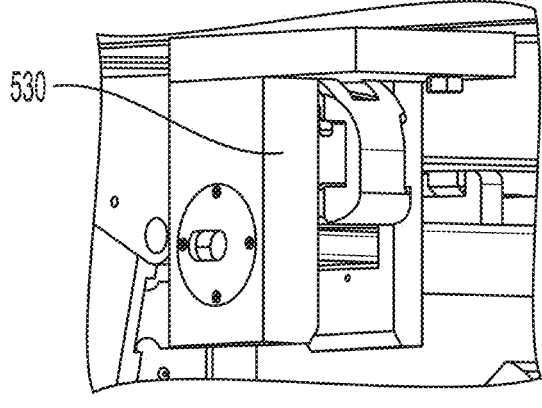
FIG. 5B shows an example of a latch.

A platform of the table top described herein may be mountable to a compatible table pedestal. A compatible table pedestal may include a table pedestal from which a table top described herein can be securely mounted. For example, should a compatible table pedestal include another table top, a user may remove the other table top and securely mount a table top as described herein. The table top described herein is mountable to a compatible table pedestal such that a front edge portion of the frame, a front edge portion of the platform, and a front edge portion of the compatible table pedestal are oriented to extend in a same direction (such as a forward direction 150 in FIG. 1). FIG. 5A shows an example of a table system comprising a platform mounted to a compatible table pedestal. In the example of FIG. 5A, a table system 500 includes a platform 510 mounted to a compatible table pedestal 512 and a frame 520 translatably mounted to the platform 510. The platform 510 can be secured to the table pedestal 512 at one or more latches 530. FIG. 5B shows an example of a latch 530.

The mounting of the table top described herein forms a table system that allows a user to configure the table system between a fully extended configuration and a fully retracted configuration. In the fully extended configuration, a front end of the frame extends at least 1 meter past a front edge portion of the platform and a front edge portion of the compatible table pedestal. The front edge portion of the platform may be a furthermost front edge of the platform. The front edge portion of the compatible table pedestal may be a furthermost front edge of the table pedestal. Capability to configure the table top between the fully extended configuration and the fully retracted configuration allows a patient on the frame to be positioned in a suitable position relative to the table pedestal for surgery and intraoperative imaging. For example, when the table system is in the fully extended configuration, a mobile imaging device aligned to the table system can scan across the patient on the projected frame.

The frame can be made of a radiolucent material, such as carbon fiber, that would not interfere or disrupt imaging of the patient. By configuring the table top in the fully extended configuration, a mobile imaging device can scan across the patient on a portion of the radiolucent frame that is extended from the front edge of the platform and the front edge of the table pedestal. In this way, the scan of the mobile imaging device can have a field of view that provides effective imaging of the patient without interference from other materials of the table system that may not be radiolucent. For example, the scan of the mobile imaging device can have a field of view that includes at least 1 meter in length across the projected frame and excludes the platform and the table pedestal.

Figures 6A, 6B:
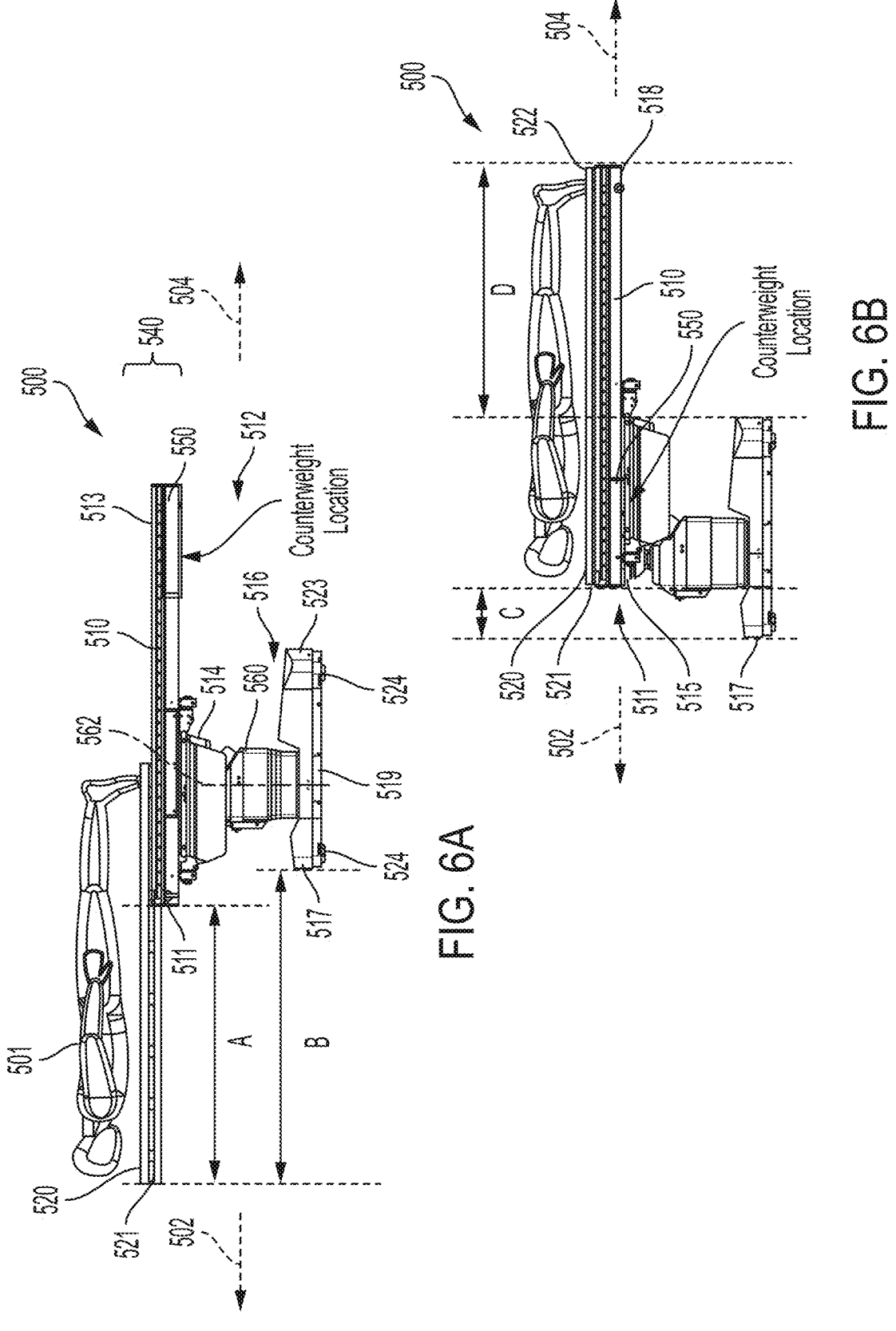
FIG. 6A shows an example of a table system in a fully extended configuration.
FIG. 6B shows an example of a table system in a fully retracted configuration.
Figure 6C:
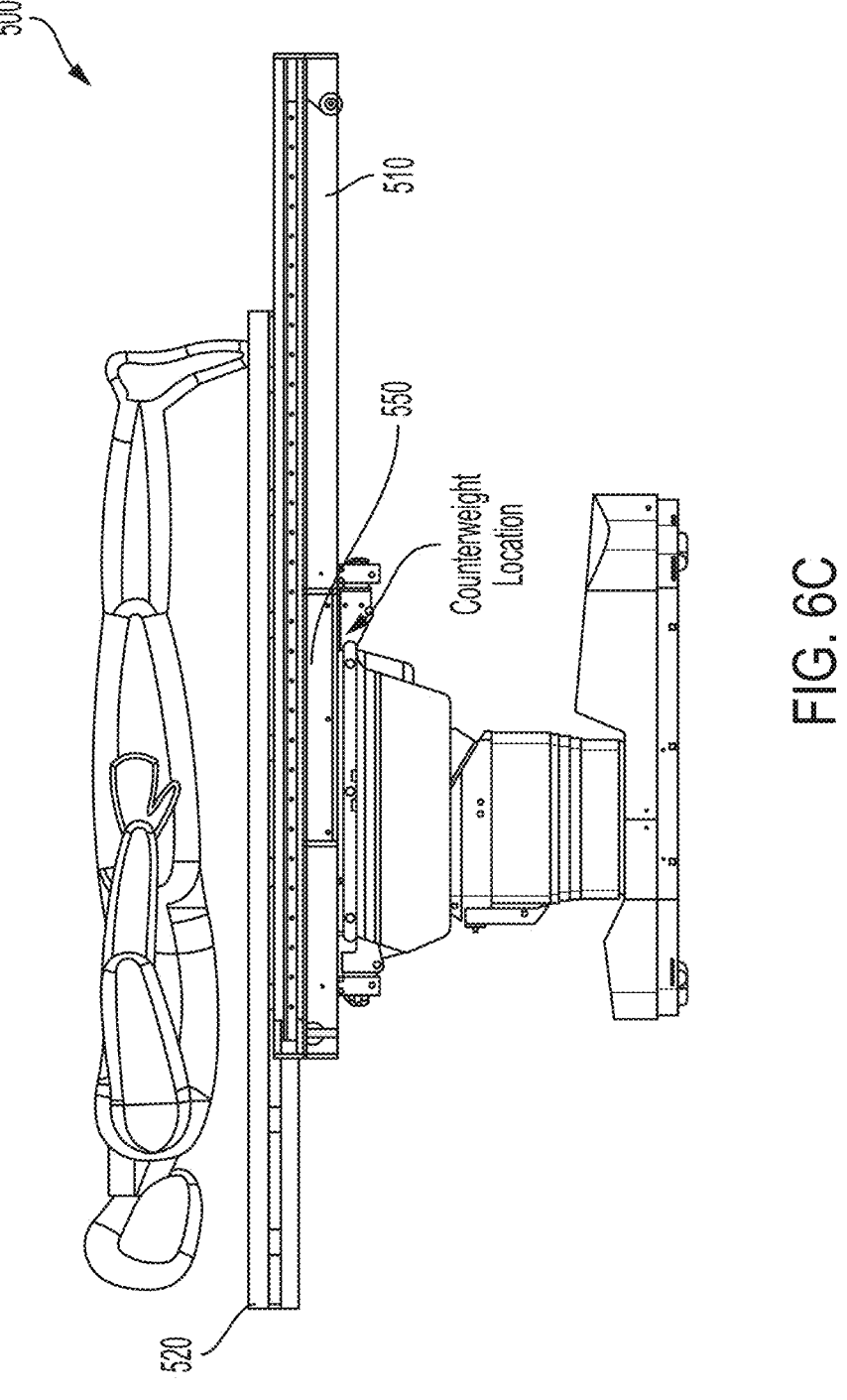
FIG. 6C shows an example of a table system in a configuration between the fully extended configuration of FIG. 6A and the fully retracted configuration of FIG. 6B.

FIGS. 6A, 6B, and 6C show examples of the table system 500 in different configurations. For reference, a patient 501 is illustrated on the frame with the patient's head positioned towards a front edge portion 521 of the frame 520. For simplicity of the illustrations, FIGS. 6A, 6B, and 6C do not show accessories mounted to the frame 520 that position the patient 501 on the frame 520. FIG. 6A shows the table system 500 in a fully extended configuration. The table system 500 includes a table top 540 comprising the platform 510 and the frame 520 and the table pedestal 512 comprising a table support 514 and a table base portion 516 attached to the table support 514. In the fully extended configuration, the front edge portion 521 of the frame 520 extends past a front edge portion 511 of the platform 510 and a front edge portion 517 of the table base portion 516. The front edge portion 521 of the frame 520, the front edge portion 511 of the platform 520, and the front edge portion 517 of the table pedestal 512 may be a respective furthermost edge portion extending in a forward direction 502 (indicated by dashed arrow) of the frame 520, the platform 510, and the table pedestal 512. In the example of FIG. 6A, lengths indicated by double arrow A and double arrow B are at least 1 meter.

The projection of the frame 520 at least 1 meter past the front edge portion 511 of the platform 510 and the front edge portion 517 of the table base portion 516 can be balanced by one or more counterweights 550 at an end portion 513 of the platform 510. According to some examples, the one or more counterweights 550 can be configured to translate in the platform 510 in a backward direction 504 (indicated by dashed arrow) opposite the forward direction 502 as the frame 520 translates to the fully extended configuration. That is, the one or more counterweights 550 may be configured to travel in an opposite direction of the frame 520.

According to some examples, a bottom 519 of the table base portion 516 has a length that extends from the front edge portion 517 of the table base portion 516 to a back edge portion 523 for helping to stabilize the table top 540 in its various configurations. According to some examples, the table pedestal 512 may be configured into an unlocked position for transporting the table pedestal 512 and in a locked position for fixing the table pedestal 512 in position. In the unlocked position, one or more wheels 524 may contact the floor. In the locked position, the one or more wheels 524 may be spaced from the floor. According to some examples, the length of the bottom end 519 may be at least 0.6 meters, or at least 0.8 meter, or at least 1 meter. According to some examples, the length of the bottom end 519 may be at most 2 meters, or at most 1.8 meters, or at most 1.6 meters. According to some examples, the length of the bottom end 519 may be 0.6 meter to 2 meters, or 0.8 meter to 1.8 meters, or 1 meters to 1.6 meters. According to some examples, the table pedestal 512 includes a column 560 that extends vertically from the table base portion 516 and the table support 514 is attached to the column 560. In some variations, a centerline 562 of the column 560 is closer to the front edge portion 517 of the table base portion 516 than to the back edge portion 523 of the table base portion 516, which may enable a mobile imaging system to be positioned closer to the centerline 562 of the column 560.

FIG. 6B shows an example of the table system 500 in a fully retracted configuration. In the fully retracted configuration, the frame 520 and the platform 510 are positioned such that the frame 520 provides clearance for a mobile imaging device to be aligned to the table system 500 without disrupting a position of the table top 540, a patient on the table top 540, and the table pedestal 512. Specifically, in the fully retracted configuration, the front edge portion 521 of the frame 520 and the front edge portion 511 of the platform 510 do not extend past the front edge portion 517 of the table base portion 516. In the example of FIG. 6B, a front retracted distance of the front edge portion 521 of the frame 520 and the front edge portion 511 of the platform 510 from the front edge portion 517 of the table base portion 516 is indicated by double arrow C and a back retracted distance of a back edge portion 522 of the frame 520 and a back edge portion 518 of the platform 510 is indicated by double arrow D.

According to some examples, the front retracted distance (indicated by double arrow C) can be at least 50 millimeters, or at least 100 millimeters, or at least 200 millimeters. According to some examples, the front retracted distance can be at most 600 millimeters, or at most 500 millimeters, or at most 400 millimeters. According to some examples, the front retracted distance can be 50 millimeters to 600 millimeters, or 100 millimeters to 500 millimeters, or 200 millimeters to 400 millimeters.

According to some examples, the back retracted distance (indicated by double arrow D) can be at least 0.8 meters, or at least 1 meter, or at least 1.1 meters. According to some examples, the back retracted distance may be at most 2 meters, or at most 1.8 meters, or at most 1.6 meters. According to some examples, the back retracted distance may be 0.8 meter to 2 meters, or 1 meter to 1.8 meters, or 1.1 meters to 1.6 meters.

According to some examples, the frame 520 and the platform 510 in the fully retracted configuration can be balanced by the one or more counterweights 550 at a front portion 515 of the platform 510. According to some examples, the one or more counterweights 550 can be configured to translate in the platform 510 in the forward direction 502 (indicated by dashed arrow) opposite the backward direction 504 as the frame 520 translates to the fully retracted configuration.

According to some examples, the table support 514 can be translatably attached to the table base portion 516. A range of movement of the table support 514 relative to the table base portion 516 is illustrated by the different positions of the table support 514 in FIGS. 6A and 6B. According to some examples, a range of the table support 514 can be between 100 to 500 millimeters. In other examples, the table support 514 is fixed relative to the table base portion 516.

FIG. 6C shows an example of the table system 500 in a configuration between the fully extended configuration of FIG. 6A and the fully retracted configuration of FIG. 6B. There may be a plurality of configurations between fully retracted configuration and the fully extended configuration. According to some examples, the plurality of configurations may be continuously or discretely spaced between the fully retracted configuration and the fully extended configuration. In the example of FIG. 6C, the one or more counterweights 550 is positioned in a more centralized position in the platform 510 compared to the fully extended configuration shown in FIG. 6A and the fully retracted configuration shown in FIG. 6B.

Figure 7:
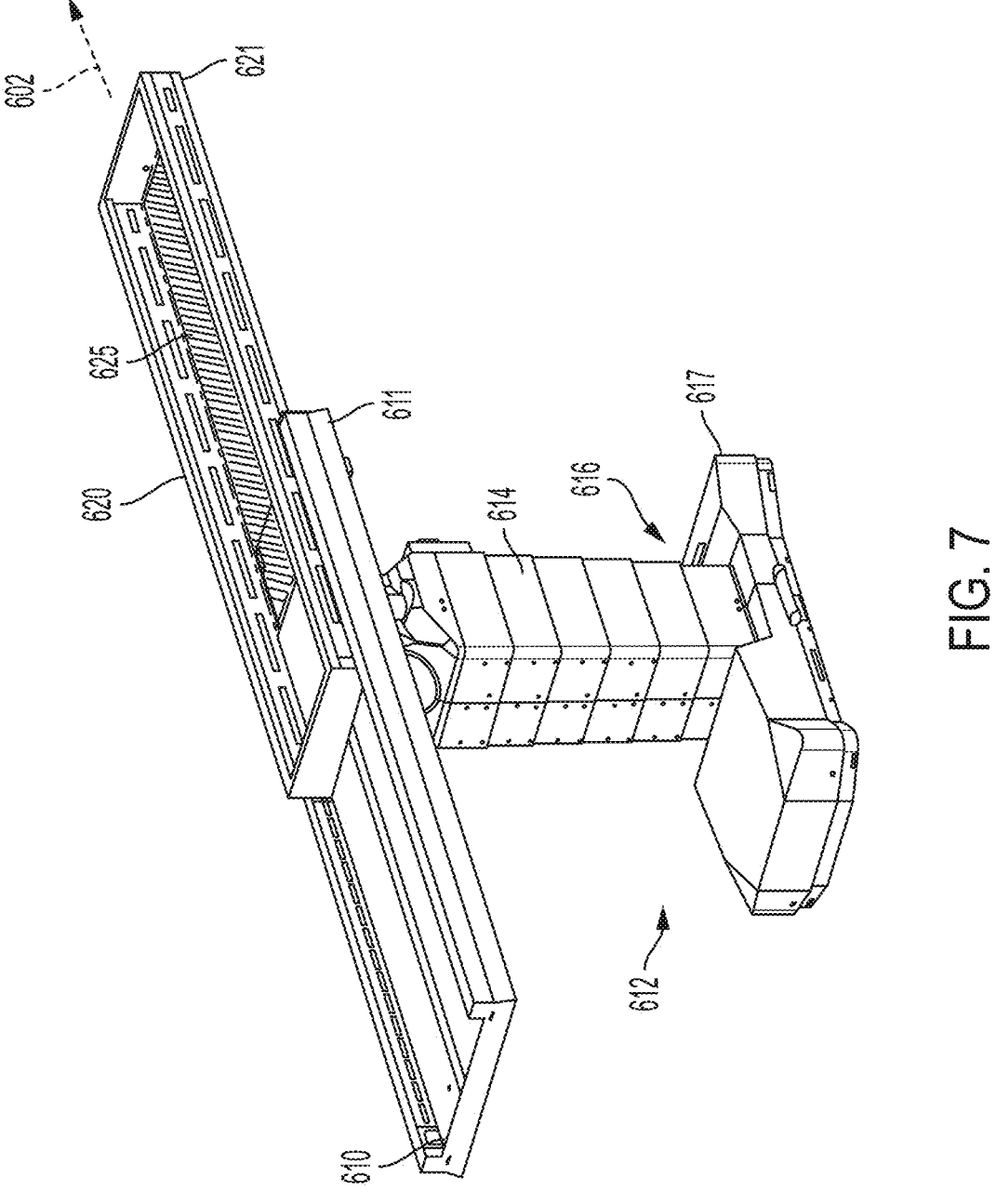
FIG. 7 shows an example of a table system that includes a platform, a frame translatably attached to the platform.

A table system can include a table top supported by a dedicated table pedestal. In some examples, the table top and table pedestal are permanently affixed to one another (i.e., the table top and pedestal are not designed to be removed from one another in the field). Similar to compatible table pedestals described herein, the dedicated table pedestal may include a table support and a table base portion. FIG. 7 shows an example of a table system 600 that includes a platform 610, a frame 620 translatably attached to the platform 610. In the example of FIG. 7, the platform 610 is attached to a dedicated table pedestal 612 that includes a table support 614 and a table base portion 616. As described in reference to table system 500, the table system 600 can be configured between a fully extended configuration and a fully retracted configuration, and configurations therebetween. In the fully extended configuration, a front edge portion 621 of the frame 620 extends at least 1 meter past a front edge portion 611 of the platform and a front edge 617 of the table base portion 616. For additional details regarding the different configurations, the reader is referred to discussions of the configurations of table system 500. Optionally, the frame 620 can include a plate 625 that can prevent a patient's body from hanging beyond a bottom of the frame 620, which could otherwise create a potential pinch hazard to the patient when translating the frame 620. The plate 625 may be removable or may be permanently installed.

A mobile imaging device may be aligned to a table system described herein for intraoperative imaging of a patient on the table system. Alignment of a mobile imaging device to the table system can include positioning the mobile imaging device such that a side of the mobile imaging device faces a front end portion of a table base portion of the table system and is within a clearance distance away from the front end portion of the table base portion of the table system, and then rotating a portion of the mobile imaging device such that the side of the mobile imaging device no longer faces the front end of the table base portion of the table system.

Figure 8A:
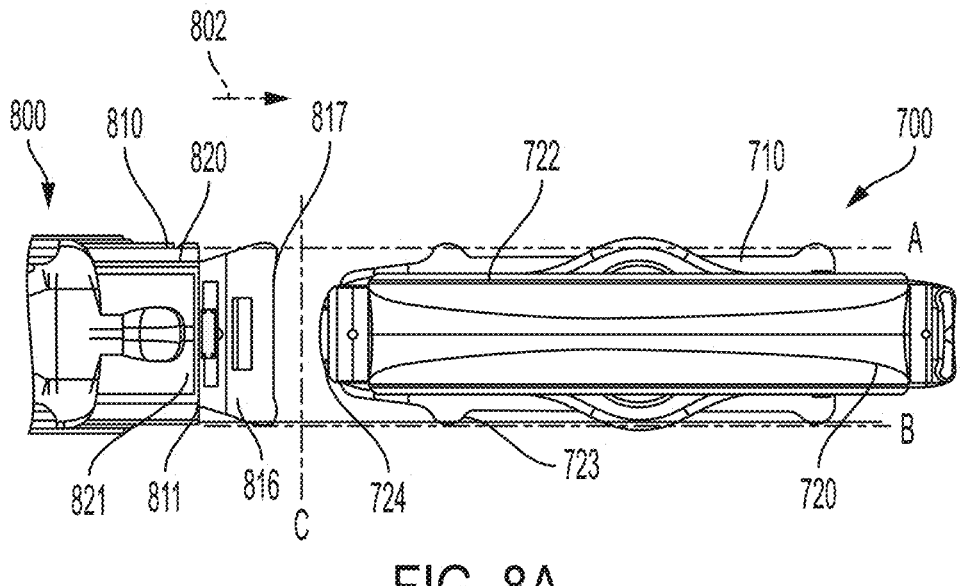
FIG. 8A shows an example of an alignment side of a mobile imaging device aligned to face a table system.

FIG. 8A shows an example of an alignment side of a mobile imaging device 700 aligned to face a table system 800. The table system 800 includes a platform 810 mounted and a frame 820 translatably mounted to the platform 810. The platform 810 can be attached to a table pedestal. According to some examples, the table system 800 comprises the table pedestal 812. The table pedestal 812 can be either a compatible table pedestal or a dedicated table pedestal as described above. According to some examples, a front portion of the table system can include a front edge portion 811 of the platform 810, a front edge portion 821 of the frame 820, and a front edge portion 817 of the table pedestal 812. These respective front edges may be furthermost edges of the platform 810, the frame 820, and the table pedestal 812 in a forward direction (indicated by dashed arrow 802). The mobile imaging device 700 includes an imaging base 710 and a scanning gantry 720 rotatably mounted to the imaging base 710. The scanning gantry 720 is configured to move (such as translation and/or rotation) an opening 722 in the scanning gantry 720 about a table system for scanning a patient on the table system. To position the opening 722 for scanning about the table system 800, an alignment side 724 of the mobile imaging device 700 can be aligned to face the front portion of a table system 800. In the example of FIG. 8A, the alignment side 724 is aligned to face the front edge portion 811 of the platform 810, the front edge portion 821 of the frame 820, and the front edge portion 817 of the table pedestal 812.

Alignment of the alignment side of the mobile imaging device to face a front portion of the table system includes positioning the alignment side of the mobile imaging device at a clearance distance from the front portion of the table system. The clearance distance can be configured to provide enough room between the table system and the mobile imaging device such that the scanning gantry 720 can be rotated relative to the imaging base 710 without contacting the table system or a patient on the table system. According to some examples, during alignment of the mobile imaging device to the table system, the table system can be configured in the fully retracted configuration to allow the mobile imaging device to be positioned at the clearance distance and the scanning gantry to rotate relative to the imaging base without contacting the frame, the platform, or the patient.

The table system 800 may include an alignment system configured to provide alignment guidance to a driver of the mobile imaging device. The alignment system may indicate at least a partial perimeter (or grid) of where a driver should position or park the mobile imaging device in a parking spot. The partial perimeter may be, for example, one or more parallel lines and one or more lines perpendicular to the one or more parallel lines. According to some examples, the alignment system may include one or more lasers configured to at least partially illuminate a perimeter of the parking spot. FIG. 8A shows an example of a partial perimeter of a parking spot represented by dash-dot lines A, B and C. In the example of FIG. 8A, lines A and B represent a width of the parking spot and the mobile imaging device should be centered in the width of the parking spot for alignment to the table system 800. Line C indicates a clearance distance of the mobile imaging device 700 from the table system 800 for alignment. That is, the alignment side 724 can be positioned up to line C to allow the scanning gantry 720 enough clearance during rotation. In some examples line C is aligned with the front edge portion 817 of the table pedestal 812. According to some examples, the clearance distance may be based on the frame 820 and the platform 810 in a fully retracted configuration (as shown in FIG. 6B). According to some examples, the dash-dot lines A, B, and C may represent laser lines visible to a user.

Figure 8B:
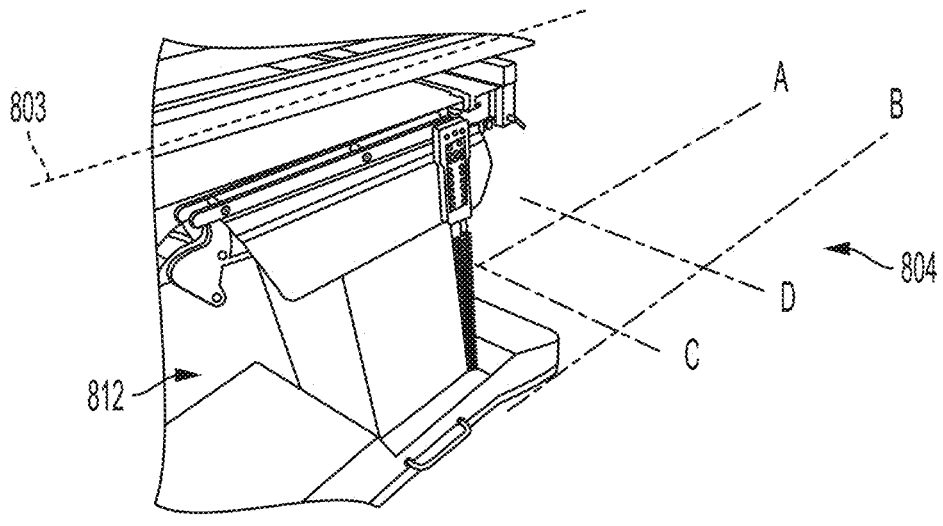
FIG. 8B shows an example of a partial perimeter parking spot and a driving guide line.

The alignment system may be configured to indicate a driving guide line in addition to at least a partial perimeter of a parking spot. FIG. 8B shows an example of a partial perimeter parking spot and a driving guide line. Similar to FIG. 8A, lines A and B of FIG. 8B indicate a width of a parking spot and line C of FIG. 8B indicates a clearance distance from the table system. Line D of FIG. 8B indicates a driving guide line. According to some examples, line D may represent a laser line visible to a user. A user may rely on the driving guide line D to drive a mobile imaging device orthogonal to a longitudinal axis 803 of the table top. For example, given the orientation of FIG. 8B and a mobile imaging device being driven in direction 804, a user may drive the mobile imaging device 700 along D such that a left side (such as side 723 aligned with line B in FIG. 8A) of the mobile imaging device drives on the line D or slightly left or right of line D. When the user drives the mobile imaging 700 such that an alignment side 724 reaches line A, a user may pivot the entire mobile imaging device (scanning gantry 720 along with imaging base 710) about the leading end portion that includes the alignment side 724 of the mobile imaging device 700. After pivoting the mobile imaging device 700, the mobile imaging device 700 would be aligned within the parking spot as shown in FIG. 8A. According to some examples, a user may adjust positioning of the mobile imaging device 700 relative to the clearance distance represented by line C as needed. Alignment of a mobile imaging device to table systems described does not require physical attachment to the table systems and therefore allows a user to align a mobile imaging device to a table system for intraoperative imaging and move the mobile imaging device away from the table system upon completion of intraoperative imaging.

Figure 9:
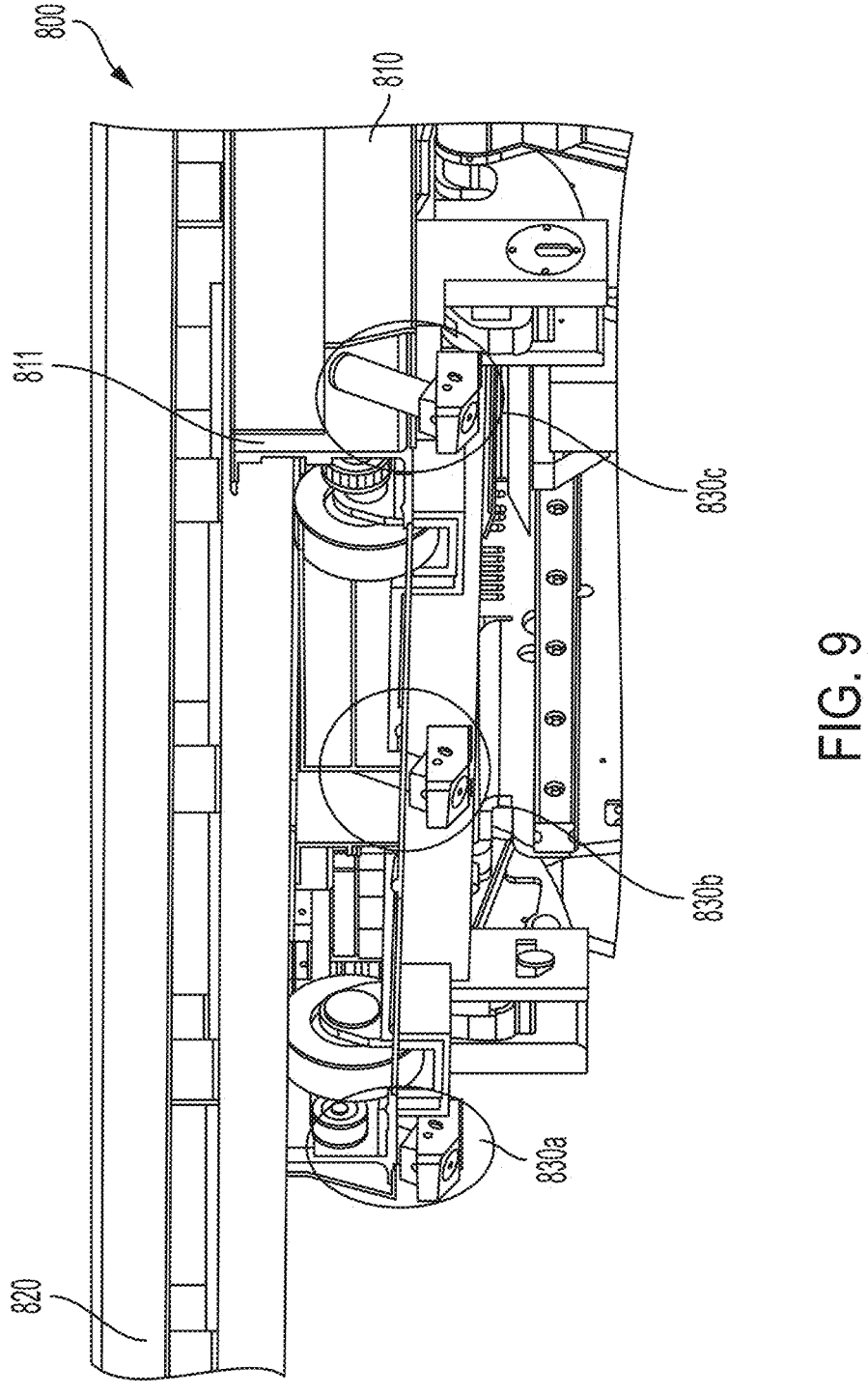
FIG. 9 shows part of an exemplary table top comprising a platform, a frame translatably mounted to the platform, and one or more aligners positioned on the platform.

The alignment system may be positioned on a table system for indicating a parking spot on a floor (as shown in FIGS. 8A and 8B). FIG. 9 shows part of an exemplary table top comprising the platform 810, the frame 820 translatably mounted to the platform 810, and one or more aligners 830*a-c* of the alignment system positioned on the platform 810. According to some examples, the one or more aligners 830*a-c* may be positioned at a front edge portion 811 of the platform 810. According to some examples, the one or more aligners 830*a-c* may be positioned at one or more locations such as a front face, a lateral face, or a bottom face of the platform 810 at the front edge portion 811. In the example of FIG. 9, aligner 830*a* is positioned on a first side of the front edge portion 811, aligner 830*c* is positioned on a second side opposite the first side of the front edge portion 811, and aligner 830*b* is positioned on a bottom face of the front edge portion 811 between aligners 830*a*, 830*c*. Each aligner may be configured to indicate a different portion of a parking spot perimeter. For example, aligner 830*a* and aligner 830*c* could indicate a width of the parking spot (as shown by lines A and B of FIG. 8A) and aligner 830*b* can indicate a clearance distance between the mobile imaging device and the table system (as shown by line C of FIG. 8A) or a driving guide (as shown by line D of FIG. 8B). As noted above, one or more of the aligners 830*a-c* can include a laser. In some variations, an aligner includes a laser in combination with one or more optics that spreads the laser from a point to a line.

Figure 10:
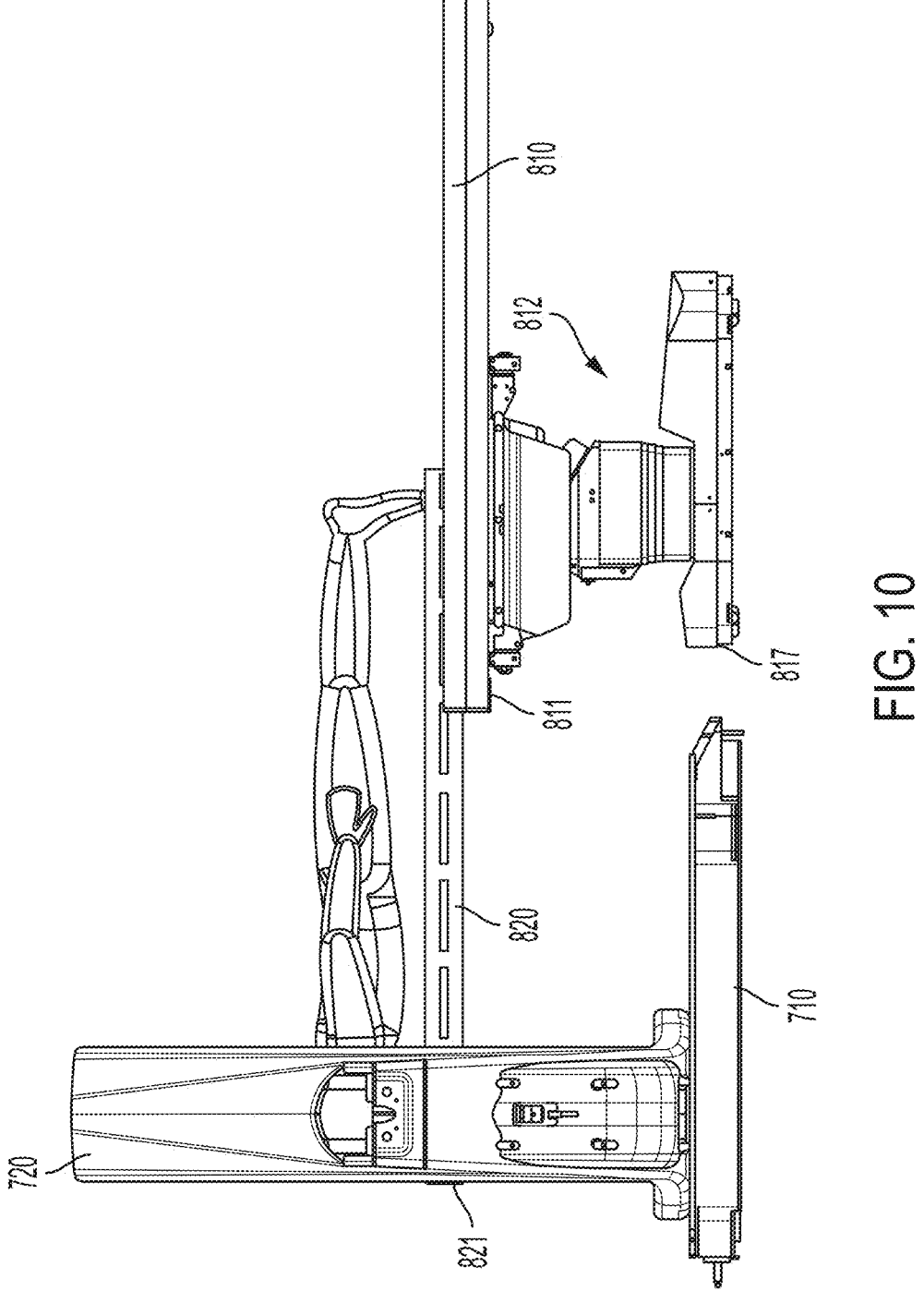
FIG. 10 shows an example of a scanning gantry positioned such that an opening of the scanning gantry faces a table system.

After an alignment side of the mobile imaging device is aligned to face a front portion of a table system at the clearance distance, the scanning gantry can be rotated such that the opening in the scanning gantry faces the table system. For example, to face the opening 722 of the scanning gantry 720 towards the table system 800, a user can rotate the scanning gantry 720 relative to the imaging base 710 about 90 degrees. When the opening 722 of the scanning gantry 720 faces the table system 800, a user may actuate translation of the scanning gantry 720 to a furthermost position on the imaging base 710, actuate translation of the frame 820 into the fully extended configuration, and actuate movement (translation and/or rotation) of the scanning gantry 720 along the imaging base 710 and about the platform 810 and the frame 820 of the table system 800 in the fully extended configuration. FIG. 10 shows an example of the scanning gantry 720 positioned such that an opening 722 of the scanning gantry 720 faces the table system 800, according to some examples. In the example of FIG. 10, the scanning gantry 720 is in a furthermost position (away from the table system) and the frame 820 and the platform 810 are configured in the fully extended configuration. As described above, in the fully extended configuration, a front edge portion 821 of the frame 820 extends at least 1 meter past the front edge portion 811 of the platform and the front edge portion 817 of the table pedestal 812. For reference, a patient is illustrated on the frame 810 with the patient's head positioned towards a front edge portion 821 of the frame 820. For simplicity of the illustrations, FIG. 10 does not show accessories mounted to the frame 820 that position the patient on the frame 820.

In some variations, the table system may be locked in place prior to aligning the mobile imaging device to the table system. For example, wheels of the pedestal of the table system may be retracted such that the pedestal is no longer supported by the wheels.

Figures 11A, 11B:
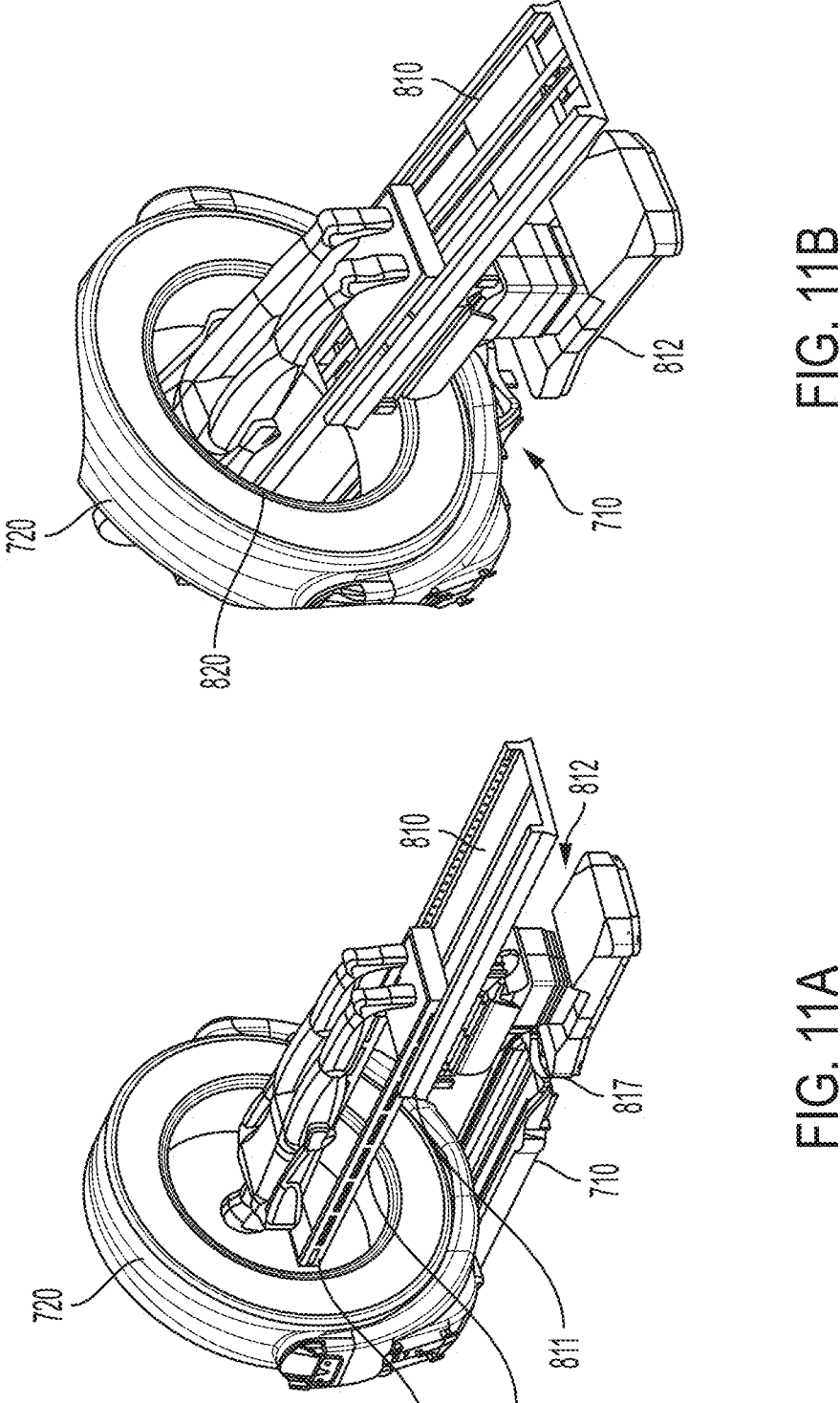
FIG. 11A shows a perspective view of an exemplary mobile imaging device in a first position and an exemplary table system.
FIG. 11B shows a perspective view of an exemplary mobile imaging device in a second position and an exemplary table system.

FIG. 11A shows a perspective view of the exemplary mobile imaging device 700 and the exemplary table system 800 of FIG. 10. In the example of FIG. 11A, the scanning gantry 720 of the mobile imaging device 700 is in a furthermost position (away from the table pedestal 812) on the imaging base 710. A user may actuate the scanning gantry 720 to move along the imaging base 710 to an innermost position relative to the table pedestal 812 as shown in the example of FIG. 11B. For simplicity of the illustrations, FIGS. 11A and 11B do not show accessories mounted to the frame 820 that position the patient on the frame 820. The distance from the furthermost position of the scanning gantry 720 and the innermost position of the scanning gantry 720 relative to the table pedestal 812 can be at least 1 meter. According to some examples, the table system 800 in the fully extended configuration can be configured such that travel of the mobile imaging device from the furthermost position to the innermost position relative to the table pedestal 812 scans the patient on the cantilevered frame 820 and does not scan or contact other portions of the table system 800. According to some examples, the frame 820 may include an alignment mark such that would indicate the innermost position of the scanning gantry 720 based on a proper alignment of the mobile imaging device 700 to the table system 800.

FIG. 12 shows an exemplary flow chart that describes a method 1200 for using a surgical table top configurable for medical imaging and supported by a table pedestal. Method 1200 may be used for table tops such as table tops of table systems 500, 600, 800.

At step 1210, a patient may be positioned on a frame of the surgical table top. The frame can be translatably attached to a platform of the surgical table top. The platform can be removably mounted on the table pedestal or can be permanently affixed to the table pedestal.

At step 1220, the frame can be linearly translated relative to the platform to a fully extended configuration in which a front edge of the frame projects at least 1 meter past a front edge of the platform and a front edge of the table base portion. According to some examples, the fully extended configuration can be configured for medical imaging. According to some examples, the front edge of the frame can be retracted in a backward direction to a fully retracted configuration in which the frame does not project from the platform past the front edge of the platform. The fully retracted configuration may be useful, for example, for aligning a mobile imaging device with the surgical table top and/or for transporting the table system.

In some examples, one or more counterweights can be translatably mounted in the platform and the projection of the front edge of the frame at least 1 meter past the front edge of the platform and the front edge of the table base portion can be balanced by translating the one or more counterweights relative to the platform based on movement of the frame. According to some examples, the one or more counterweights in the platform can be configured to move in an opposite direction than the frame in response to actuation of the frame, or vice versa.

A front portion of the surgical table top and the table pedestal can include the front edge of the platform, the front edge of the frame, and the front edge of the table base portion. The front portion can be positioned to face a mobile medical imaging device, wherein in the fully extended configuration the front edge of the frame and the front edge of the platform project past the front edge of the table base portion in a forward direction away from a back portion of the surgical table top and the table pedestal. In contrast, in the fully retracted configuration the front edge of the frame and the front edge of the platform do not extend past the front edge of the table base portion in the forward direction.

A plurality of lasers can be powered to at least partially outline a site for positioning a mobile gantry for medical imaging at the front end of the table base portion. The site can be considered a parking spot for the mobile gantry.

The table pedestal can include a table base portion and a table support attached to the table base portion. According to some examples, the table support can be translatably attached to the table base portion. According to some examples, one or more accessories can be attached to one or more rails of the frame for positioning the patient on the frame. According to some examples, the table base portion can include one or more wheels and the one or more wheels may be configured to contact the floor when the table base portion is in an unlocked position and configured to be spaced from the floor when the table base portion is in a locked position.

FIG. 13 shows an exemplary flow chart that describes a method 1300 for aligning a mobile imaging device to a surgical table top. The surgical table top can be mountable to a table pedestal and configured for positioning a patient on the surgical table top. According to some examples, the table pedestal can include a table base portion and table support mounted to the table base portion, and the surgical table top can include a platform mounted to the table support and a frame translatably mounted to the platform. Method 1300 may be used for aligning mobile imaging devices to table tops such as table tops of table systems 500, 600, 800.

At step 1310, one or more first lasers positioned at a first location on the surgical table top can be powered to emit light that at least partially outlines a first portion of a site in which to position the mobile device for medical imaging of the patient positioned on the surgical table top. At step 1320, one or more second lasers positioned at a second location on the surgical table top can be powered to emit light that at least partially outlines a second portion of the site. The one or more second lasers can be configured to emit light in a direction perpendicular to the one or more first lasers.

The first location and the second location can be one or more of a bottom side, a front edge, or a lateral edge of the surgical table top. The front edge of the surgical table top can be configured to be positioned closer to the medical imaging device than a back edge of the surgical table top opposite the front edge.

The mobile imaging device can be positioned in the site. The site may include a first mark that indicates a first distance to space the mobile imaging device from the surgical table top. A user driving the mobile imaging device can move the mobile imaging device towards the surgical table top to the first mark. According to some examples, the surgical table top can include an alignment mark. Movement of the mobile device to the first mark allows a scan length of the mobile device from the front edge of the surgical table top to the alignment mark on the surgical table top.

According to some examples, the one or more counterweights in a platform of a table described herein may be fixed in the platform. The one or more fixed counterweights can be positioned in the platform such that a table top comprising the platform and a frame translatably mounted to the platform can be balanced on a table pedestal regardless of a configuration of the table top to reduce the load to the table pedestal and avoid tipping. For example, the one or more counterweights may be fixed in position such that a projection of a front edge portion of the frame past a front edge portion of the platform and a front edge portion of the pedestal is balanced. The projection of a fully extended configuration may be in a forward direction. The same position of the one or more counterweights may also balance the frame and the platform on table pedestal when the front edge portion of the frame is fully retracted in an opposite direction to the forward direction—that is, when the frame is in a fully retracted configuration. The one or more counterweights can be fixed in position relative to the platform in any suitable location. In some examples and with reference to FIG. 7, the one or more fixed counterweights may be located in vertical alignment with the pedestal 614.

The foregoing description, for the purpose of explanation, has been described with reference to specific examples.

However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A surgical table top configurable for medical imaging, the table top comprising:
   a platform mountable to a table pedestal;
   a frame translatably mounted to the platform, wherein the frame and the platform are linearly translatable between a fully extended configuration and a fully retracted configuration, and in the fully extended configuration, a front edge of the frame projects from the platform at least 1 meter past a front edge of the platform; and
   one or more counterweights translatably mounted to the platform, wherein translation of the frame is balanced by the one or more counterweights, and wherein the one or more counterweights translate relative to the platform in a direction opposite of the translation of the frame;
   an actuator configured to linearly translate the frame relative to the platform between the fully extended configuration and the fully retracted configuration,
   wherein the fully extended configuration is configured for medical imaging.

2. The surgical table top of claim 1, wherein the actuator comprises an actuator mechanism attached to the frame and to the one or more movable counterweights, the actuator mechanism comprising at least one or more of a pulley, worm drive, hypoid drive, and rack and pinion, wherein movement of the actuator mechanism is configured to move the one or more movable counterweights in an opposite direction than the frame when the actuator moves the frame relative to the platform.

3. The surgical table top of claim 1, wherein in the fully retracted position the frame does not project from the platform past the front edge of the platform.

4. The surgical table top of claim 1, wherein the platform has a fixed length and maintains the fixed length between the fully extended configuration and the fully retracted configuration.

5. The surgical table top of claim 1, wherein the table pedestal comprises a table base portion and a table support that is mounted to the table base portion, and a front portion of the surgical table top and the table pedestal includes the front edge of the platform, the front edge of the frame, and a front edge of the table base portion, and the front portion is configured to face a mobile medical imaging device, wherein in the fully extended configuration the front edge of the frame and the front edge of the platform project past the front edge of the table base portion in a forward direction away from a back portion of the surgical table top and the table pedestal, and in the fully retracted configuration the front edge of the frame and the front edge of the platform do not extend past the front edge of the table base portion in the forward direction.

6. The surgical table top of claim 1, wherein the table pedestal comprises a table base portion and a table support mounted to the table base portion, the table base portion comprising one or more wheels configured to contact the floor when the table base portion is in an unlocked configuration and configured to be spaced from the floor when the table base portion is in a locked position, and wherein the table support is configured to linearly translate relative to the table base portion.

7. The surgical table top of claim 6, wherein the platform comprises a length that is longer than a length of the table base portion that is configured to contact the floor.

8. The surgical table top of claim 1, wherein the frame comprises opposite facing rails and opposite facing end plates that form an opening over which a patient is to be positioned.

9. The surgical table top of claim 1, wherein the frame comprises one or more indicators to mark a length to which a mobile medical imaging device can scan along the frame when the mobile medical imaging device is properly aligned with the surgical table top.

10. The surgical table top of claim 1, wherein the frame comprises one or more rails configured to attach one or more accessories for positioning the patient on the frame.

11. The surgical table top of claim 1, wherein the actuator is configured to linearly translate and lock the frame and the platform in any configuration between the fully extended configuration and the fully retracted configuration.

12. The surgical table top of claim 1, wherein the frame is made of a radiolucent material.

13. The surgical table top of claim 12, wherein the radiolucent material is carbon fiber.

14. The surgical table top of claim 1, wherein the surgical table top and the table base are sized to fit through a standard door opening.

15. The surgical table top of claim 1, comprising an aligner configured to at least partially outline a site in which to position a mobile gantry for medical imaging of the patient positioned on the frame.

16. The surgical table top of claim 1, comprising a plurality of lasers configured to emit light that at least partially outlines a site in which to position a mobile gantry for medical imaging of the patient positioned on the frame.

17. The surgical table top of claim 1, wherein the plurality of lasers are positioned at the front edge of the platform on a bottom side or a lateral side of the platform.

18. The surgical table top of claim 17, wherein the plurality of lasers comprises one or more first lasers and one or more second lasers, the one or more first lasers are configured to emit light in a direction perpendicular to the one or more second lasers.

19. A mobile radiolucent table system configurable for medical imaging, comprising a table pedestal comprising a table base portion and a table support mounted to the table base portion; and the surgical table top of claim 1, wherein the platform is mounted to the table pedestal.

20. A method of using a surgical table top configurable for medical imaging and mountable to a table pedestal, the table pedestal comprising a table base portion and a table support attached to the table base portion, the method comprising:
    positioning a patient on a frame of the surgical table top, wherein the frame is translatably mounted to a platform of the surgical table top and the platform is mounted on the table support, wherein a centerline of the table support is closer to a front end of the table base portion compared to a back end of the table base portion; and
    linearly translating the frame relative to the platform to a fully extended configuration in which a front edge of the frame projects from the platform at least 1 meter past a front edge of the platform and a front edge of the table base portion, wherein the fully extended configuration is configured for medical imaging, wherein translation of the frame causes translation of one or more counterweights translatably mounted to the platform in a direction opposite of the translation of the frame.

21. The method of claim 20, comprising retracting the front edge of the frame in a backward direction to a fully retracted configuration in which the frame does not project from the platform past the front edge of the platform.

22. The method of claim 20, wherein a front portion of the surgical table top and the table pedestal includes the front edge of the platform, the front edge of the frame, and the front edge of the table base portion, and the method comprising positioning the front portion to face a mobile medical imaging device, wherein in the fully extended configuration the front edge of the frame and the front edge of the platform project past the front edge of the table base portion in a forward direction away from a back portion of the surgical table top and the table pedestal, and in the fully retracted configuration the front edge of the frame and the front edge of the platform do not extend past the front edge of the table base portion in the forward direction.

23. The method of claim 22, comprising powering a plurality of lasers to at least partially outline a site for positioning a mobile gantry at the front end of the table base portion.

24. The method of claim 22, comprising positioning a mobile gantry at the front end of the table base portion.

25. The method of claim 20, comprising attaching one or more accessories to one or more rails of the frame for positioning the patient on the frame.

26. An alignment system of a surgical table top, the surgical table top being mountable to or mounted to a table pedestal and configured for positioning a patient on the surgical table top, the alignment system comprising:
    a first aligner mounted to the surgical table top, the first aligner comprising at least one laser and optics configured to form a line on a surface that at least partially outlines a site on the surface on which to position a mobile device for medical imaging of the patient positioned on the surgical table top.

27. The alignment system of claim 26, wherein the table pedestal comprises a table base portion and table support mounted to the table base portion, and the surgical table top comprises a platform mounted to the table support and a frame translatably mounted to the platform.

28. The alignment system of claim 26, comprising a second aligner mounted to the surgical table top, the second aligner comprising at least one laser and optics configured to form another line on the surface that at least partially outlines the site.

29. The alignment system of claim 28, wherein the line formed by the second aligner is in a direction perpendicular to the line formed by the first aligner.

30. The alignment system of claim 28, wherein the first aligner is positioned at a bottom side of the surgical table top, and the second aligner is positioned at a front edge of the surgical table top, wherein the front edge of the surgical table top is configured to be positioned closer to the medical imaging device than a back edge of the surgical table top opposite the front edge.

31. The alignment system of claim 30, wherein the site comprises a first mark that indicates a first distance to space the mobile imaging device from the surgical table top.

32. The alignment system of claim 31, wherein the surgical table top comprises an alignment mark, wherein movement of the mobile imaging device to the first distance allows a scan length of the mobile device from the front edge of the surgical table top to the alignment mark on the surgical table top.

33. A method for aligning a mobile imaging device to a surgical table top that is mountable to or mounted to a table pedestal and configured for positioning a patient, the method comprising:

powering a first aligner mounted to the surgical table top, the first aligner comprising at least one laser and optics that form a line on a surface that at least partially outlines a site on the surface on which to position the mobile device for medical imaging of the patient positioned on the surgical table top.

34. The method of claim 33, comprising positioning the mobile imaging device in the site.

35. The method of claim 33, wherein the site includes a first mark that indicates a first distance to space the mobile imaging device from the surgical table top, and the method comprising moving the mobile imaging device towards the surgical table top to the first mark.

36. The method of claim 35, wherein the surgical table top comprises an alignment mark, wherein movement of the mobile device to the first mark allows a scan length of the mobile device from the front edge of the surgical table top to the alignment mark on the surgical table top.

37. The method of claim 33, comprising positioning a patient on the surgical table top.

38. The method of claim 33, comprising powering a second aligner mounted to the surgical table top, the first aligner comprising at least one laser and optics that form another line on the surface that at least partially outlines the site.

\* \* \* \* \*